US010327960B2

(12) United States Patent
Hardie et al.

(10) Patent No.: US 10,327,960 B2
(45) Date of Patent: Jun. 25, 2019

(54) FEMININE PAD WITH BARRIER CUFFS

(71) Applicant: The Procter & Gamble Company, Cincinnati, OH (US)

(72) Inventors: Stephen LeBeuf Hardie, Mason, OH (US); Edward Paul Carlin, Deerfield Township, OH (US); Ronda Lynn Glassmeyer, Cincinnati, OH (US); Michael Dale Trennepohl, Cincinnati, OH (US); John Ferrer, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 294 days.

(21) Appl. No.: 15/241,103

(22) Filed: Aug. 19, 2016

(65) Prior Publication Data

US 2017/0049634 A1 Feb. 23, 2017

Related U.S. Application Data

(60) Provisional application No. 62/208,248, filed on Aug. 21, 2015, provisional application No. 62/250,560, filed on Nov. 4, 2015.

(51) Int. Cl.
*A61F 13/475* (2006.01)
*A61F 13/15* (2006.01)
*A61F 13/472* (2006.01)
*A61F 13/532* (2006.01)
*A61F 13/47* (2006.01)
(Continued)

(52) U.S. Cl.
CPC .......... *A61F 13/4758* (2013.01); *A61F 13/15* (2013.01); *A61F 13/475* (2013.01); *A61F 13/4752* (2013.01); *A61F 13/4753* (2013.01); *A61F 13/15642* (2013.01); *A61F 13/47272* (2013.01); *A61F 13/532* (2013.01); *A61F 13/5611* (2013.01); *A61F 2013/16* (2013.01); *A61F 2013/4708* (2013.01); *A61F 2013/530817* (2013.01); *A61F 2013/530839* (2013.01); *A61L 15/225* (2013.01); *A61L 15/425* (2013.01)

(58) Field of Classification Search
CPC ..................... A61F 13/475–4753; A61F 13/15
See application file for complete search history.

(56) References Cited

U.S. PATENT DOCUMENTS 4,556,146 A 12/1985 Swanson et al.
4,610,678 A 9/1986 Weisman et al.
(Continued)

FOREIGN PATENT DOCUMENTS

EP 1447066 A1 8/2004
JP WO 9623471 A1 * 8/1996 ....... A61F 13/15707
(Continued)

OTHER PUBLICATIONS

International Search Report and Written Opinion (PCT/US2016/047736) dated Nov. 18, 2016.
(Continued)

*Primary Examiner* — Susan S Su
(74) *Attorney, Agent, or Firm* — Geoge H. Leal

(57) ABSTRACT

A disposable absorbent article having barrier cuffs is disclosed herein. The disposable absorbent article has improved pad curl characteristics which can facilitate application of the disposable absorbent article.

33 Claims, 14 Drawing Sheets

(51) Int. Cl.
  *A61F 13/53* (2006.01)
  *A61L 15/22* (2006.01)
  *A61L 15/42* (2006.01)
  *A61F 13/56* (2006.01)

(56) References Cited

U.S. PATENT DOCUMENTS

| | | | |
|---|---|---|---|
| 4,673,402 A | | 6/1987 | Weisman et al. |
| 4,695,278 A | | 9/1987 | Lawson |
| 4,704,115 A | | 11/1987 | Buell |
| 4,795,454 A | | 1/1989 | Dragoo |
| 4,824,765 A | | 4/1989 | Sperry et al. |
| 4,834,735 A | | 5/1989 | Alemany et al. |
| 4,888,231 A | | 12/1989 | Angstadt |
| 4,909,803 A | | 3/1990 | Aziz et al. |
| 4,917,697 A | | 4/1990 | Osborn, III et al. |
| 5,147,345 A | | 9/1992 | Young et al. |
| 5,149,720 A | | 9/1992 | DesMarais et al. |
| 5,234,423 A | | 8/1993 | Alemany et al. |
| 5,287,207 A | | 2/1994 | Mulkens et al. |
| 5,500,451 A | | 3/1996 | Goldman et al. |
| 5,599,335 A | | 2/1997 | Goldman et al. |
| 5,810,800 A | * | 9/1998 | Hunter .............. A61F 13/4753 604/358 |
| 5,827,909 A | | 10/1998 | DesMarais |
| 6,160,028 A | | 12/2000 | Dyer |
| 6,315,765 B1 | * | 11/2001 | Datta .............. A61F 13/47272 604/358 |
| 6,369,121 B1 | | 4/2002 | Catalfamo et al. |
| 6,402,729 B1 | * | 6/2002 | Boberg .............. A61F 13/4753 604/385.28 |
| 6,440,112 B1 | * | 8/2002 | Glaug .............. A61F 13/4752 604/385.01 |
| 7,717,894 B2 | | 5/2010 | Ikeda et al. |
| 7,905,872 B2 | | 3/2011 | McKiernan et al. |
| 7,935,207 B2 | | 5/2011 | Zhao et al. |
| 8,419,701 B2 | | 4/2013 | McKiernan et al. |
| 2005/0140057 A1 | | 6/2005 | Gerndt |
| 2006/0142724 A1 | * | 6/2006 | Watanabe .......... A61F 13/4702 604/385.04 |
| 2008/0319855 A1 | | 12/2008 | Stivoric et al. |
| 2009/0198204 A1 | * | 8/2009 | Kudo .............. A61F 13/4704 604/385.04 |
| 2009/0306618 A1 | * | 12/2009 | Kudo .............. A61F 13/4704 604/386 |
| 2009/0312730 A1 | | 12/2009 | LaVon et al. |
| 2010/0069870 A1 | * | 3/2010 | Cohen .............. A61F 13/4752 604/385.04 |
| 2010/0145296 A1 | * | 6/2010 | Kudo .............. A61F 13/4704 604/385.01 |
| 2010/0152696 A1 | * | 6/2010 | Kudo .............. A61F 13/4704 604/385.14 |
| 2010/0280479 A1 | * | 11/2010 | Svensson .......... A61F 13/4752 604/385.23 |
| 2011/0319855 A1 | | 12/2011 | Lash |
| 2012/0232508 A1 | * | 9/2012 | Urushihara ....... A61F 13/53436 604/365 |
| 2014/0163500 A1 | | 6/2014 | Roe et al. |
| 2014/0163506 A1 | | 6/2014 | Roe et al. |
| 2014/0163511 A1 | | 6/2014 | Roe et al. |
| 2016/0067115 A1 | * | 3/2016 | Ishikawa .......... A61F 13/15593 604/385.29 |

FOREIGN PATENT DOCUMENTS

| | | |
|---|---|---|
| WO | WO199511652 A1 | 5/1995 |
| WO | WO1996020679 A2 | 7/1996 |
| WO | WO0110372 A1 | 2/2001 |
| WO | WO2012052172A1 A1 | 4/2012 |
| WO | WO2012057332 A1 | 5/2012 |
| WO | WO2014188301 A1 | 11/2014 |

OTHER PUBLICATIONS

International Search Report and Written Opinion (PCT/US2016/047738) dated Nov. 17, 2016.
International Search Report and Written Opinion filed Nov. 18, 2016 (PCT/US2016/047740.
ADMET: "Materials Testing Guide", Jul. 1, 2013, http://cdn2.hubspot.net/hub/10514/file-236488676-pdf/ADMET_Materials_Testing_Guide_July_2013.pdf.
U.S. Appl. No. 15/241,107, filed Aug. 19, 2016, Hardie et al.
U.S. Appl. No. 15/241,110, filed Aug. 19, 2016, Hardie et al.
All Office Actions for U.S. Appl. No. 15/241,107, filed Aug. 19, 2016.
All Office Actions for U.S. Appl. No. 15/241,110, filed Aug. 19, 2016.

* cited by examiner

FEMININE PAD WITH BARRIER CUFFS

FIELD

The present invention pertains to feminine disposable absorbent articles comprising barrier cuffs.

BACKGROUND

Disposable absorbent articles having barrier cuffs are currently on the market. For example, many brands of disposable diaper employ barrier cuffs to help reduce the likelihood of leakage. In general, the barrier cuffs comprise a pre-strained elastic strand or plurality thereof which cause the barrier cuff to stand up when the diaper is in use. Without the feature of standing up, the barrier cuffs would be relatively ineffective at preventing or reducing the likelihood of leakage.

Typically, diapers are folded when packaged. In most instances, packaged diapers are folded along what is generally a lateral centerline which bisects the length of the diaper. Because the elastic of the barrier cuff is pre-strained, the barrier cuff urges the diaper into its folded state. In donning the diaper on a wearer, the pre-strained elastics help urge the diaper onto the body and can help conform the diaper thereto.

In the feminine article context, particularly sanitary napkins or feminine pads, barrier cuffs are not as prevalent as they are with diapers. But similar to diapers, barrier cuffs for feminine pads also include pre-strained elastics. And, much like diapers, feminine pads are also typically folded when packaged. For example, feminine pads may be folded along a lateral centerline much like diapers, or in some instances, feminine pads may comprise multiple folds, e.g. folded in thirds. Similar to the barrier cuffs of diapers, the barrier cuffs of the feminine pads also urge the feminine pad into its folded state. However, in contrast to diapers, when donning feminine pads, the feminine pad is typically applied and adhered to the underwear of the wearer as opposed to being directly applied to the body. Because the barrier cuffs tend to urge the feminine pads into their folded state, application of the feminine pad to underwear may prove difficult. Even where the feminine pad comprises a fastening adhesive, the barrier cuff elastics may overcome the adhesive forces. And while some conventional articles attempt to abate the forces of the barrier cuff, such attempts—while mitigating the effect of the barrier cuffs regarding urging into a folded position—typically cause ends of the feminine pad to curl inward. And since, the fastening adhesive for feminine pads is typically centrally located, the ends can be difficult to uncurl during donning. Unfortunately, the difficult application of the feminine pads could dissuade consumers from purchasing feminine pads with barrier cuffs despite the added protection of the barrier cuffs.

Accordingly, there is a need for feminine pads with barrier cuffs that can facilitate application.

SUMMARY

Disposable absorbent article in accordance with the present invention can facilitate the application of the article for the wearer. For example, the application of the article into the panty of a wearer may be facilitated because of the reduced pad curl as described herein.

In some forms, disposable absorbent articles of the present invention comprises a longitudinal axis and a lateral axis perpendicular to the longitudinal axis. The disposable absorbent article further comprises a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet. A fastening adhesive is disposed on a garment-facing surface of the chassis. Additionally, a first cuff extends along the first longitudinal side edge, and a second cuff extends along the second longitudinal edge. And, the article has a flexibility factor of less than 240 and an average pad curl of less than 3.0 mm.

In some forms, a disposable absorbent article comprises a longitudinal axis and a lateral axis perpendicular to the longitudinal axis. The disposable absorbent article further comprises a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet. A fastening adhesive is disposed on a garment-facing surface of the chassis. Additionally, a first cuff extends along the first longitudinal side edge, and a second cuff extends along the second longitudinal edge. And, the article has a flexibility factor of less than 190 and an average pad curl of less than 7.5 mm.

In some forms, a disposable absorbent article comprises a longitudinal axis and a lateral axis perpendicular to the longitudinal axis. The disposable absorbent article further comprises a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet. A fastening adhesive is disposed on a garment-facing surface of the chassis. Additionally, a first cuff extends along the first longitudinal side edge, and a second cuff extends along the second longitudinal edge. And, the article has an average pad curl that satisfies the following equation:

$$APC \leq (-0.0338 FF + 8.7879).$$

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION

Figure 1:
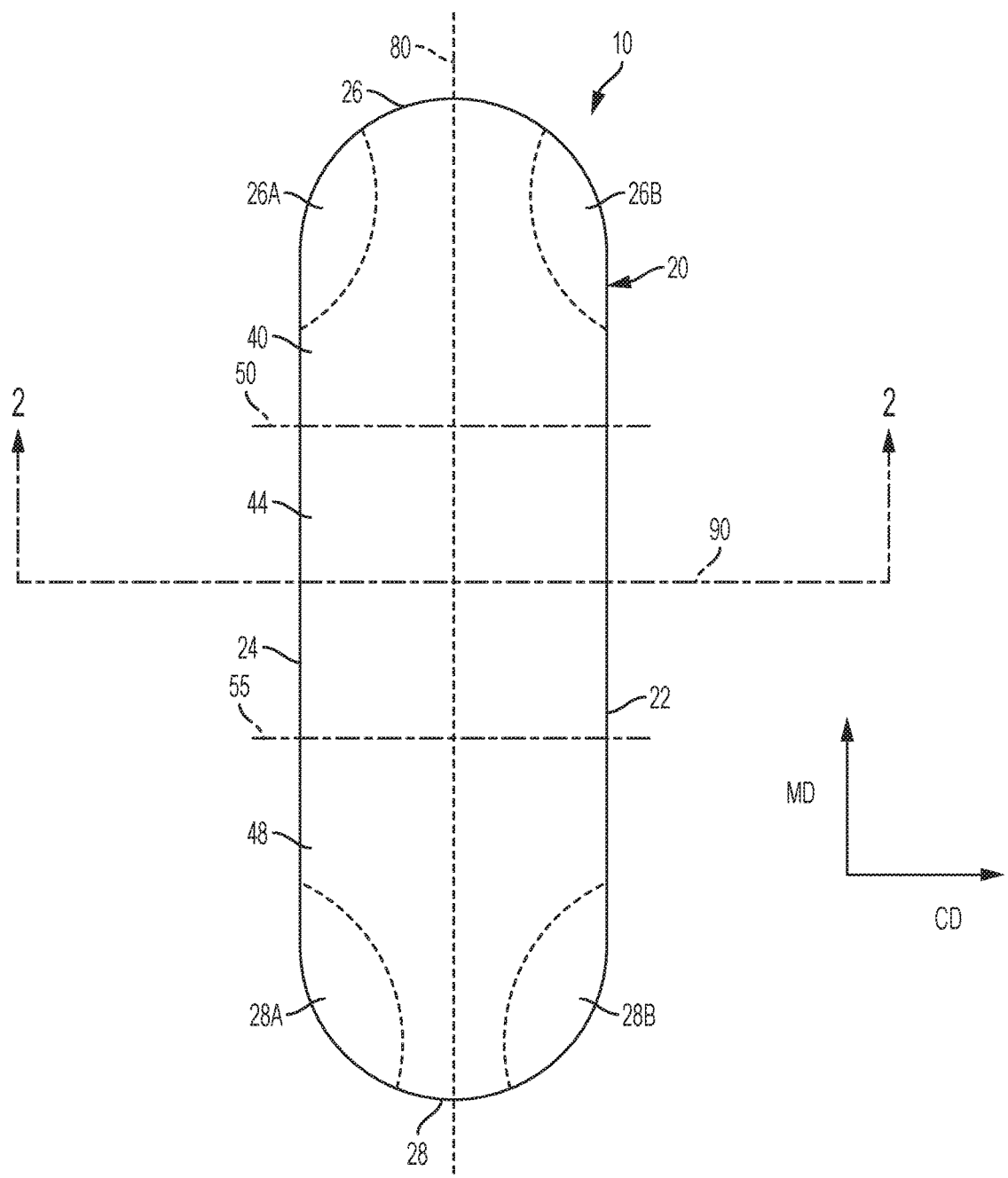
FIG. 1 is a plan view showing an exemplary embodiment of a feminine article, i.e. feminine pad.

Feminine pads of the present invention can provide flexibility to allow for a comfortable fit and can provide facilitated application to the underwear of the user. For the purposes of this disclosure, reference to a feminine pad, disposable absorbent article or absorbent article will be used. However, the present invention may be applied to a plurality of feminine articles including, but not limited to, sanitary napkins, pantiliners, adult incontinence pads, menstrual pads, etc.

There are several factors to consider when creating a feminine pad with barrier leg cuffs, particularly if the focus is facilitation of application. First, the stiffness of the pad is an important factor. Typically, thinner pads offer less stiffness than their bulkier counterparts. While bulkier pads may resist the forces exerted by the barrier cuffs, bulkier pads are less desirable because they can cause the feminine pad to lose its discreetness during use. And, some flexibility in the absorbent core can allow the feminine pad to adjust more readily to the contours of the body of a user during use. Second, the stability of the feminine pad during application is an important variable. The feminine pad ideally, should open easily and lay flat for application to the underwear of the user. The forces exerted upon the article by the barrier cuffs should be counteracted such that the feminine pad can be easily flattened without the ends of the feminine pad curling or at least a reduced amount of curling. Third, barrier cuffs associated with the feminine pad need to provide functional gasketing. Namely, the barrier cuffs need to stand up during use and contact the body of the wearer in an appropriate location to reduce the likelihood of leakage beyond the barrier cuff.

Historical designs have required sacrifice with one or more of the above factors. In contrast, feminine pads constructed in accordance with the present disclosure take into consideration all three of these factors to create a new feminine pad. Namely, feminine pads of the present disclosure can provide good core flexibility, low pad curl to facilitate application of the feminine pad, and barrier cuffs which stand up during use and contact the wearer in an appropriate location to ensure reduced likelihood of leakage from the feminine pad.

As noted previously, some flexibility of the feminine pad is desirable. For example, referring to FIG. 1, in general, a feminine pad of the present invention should have flexibility in both the cross machine direction ("CD direction") and in the machine direction ("MD direction"). The flexibility in the CD can allow the feminine pad to more readily adapt to contours of a user's body. However, more flexibility in the CD can create a potential for pad curl during application. Pad curl is the extent to which the pad, adjacent the end edges 26 and 28 curl when the pad is placed on a flat surface and fully extended thereon. Pad curl specifically operates on "corners" of the feminine pad 10. For example, corners 26A and 26B associated with end edge 26 and corners 28A and 28B associated with end edge 28 are susceptible to curl. Similarly, some flexibility in the MD direction is desirable; however, high flexibility in the MD direction can create a potential for the barrier cuff forces to fold end regions 40 and 48 of the feminine pad 10.

Still referring to FIG. 1, the feminine pad 10 is shown and may comprise a longitudinal axis 80 and a lateral axis 90. The longitudinal axis 80 generally extends parallel to the longest dimension of the feminine pad 10. The lateral axis 90 extends generally perpendicular to the longitudinal axis 80 and lies in the same plane as the feminine pad 10 in a flattened state on a flat surface. The lateral axis 90 bisects the length of the feminine pad 10 where the length is parallel to the longitudinal axis 80, and the longitudinal axis 80 bisects the width of the feminine pad 10 where the width is parallel to the lateral axis 90. Additionally, as shown, the MD direction may be generally parallel to the longitudinal axis 80 of the feminine pad 10, and the CD direction may be generally parallel to the lateral axis 90.

The feminine pad 10 may further comprise a chassis 20 comprising a plurality of side edges 22 and 24 which extend generally parallel to the longitudinal axis 80. A pair of end edges 26 and 28 join each of the side edges 22 and 24. One end edge 26 joins the side edges 22 and 24 in the first end region 40 of the feminine pad 10 while the other end edge 28 joins the side edges 22 and 24 in the second end region 48 of the feminine pad 10—the second end region 48 being opposite the first end region 40. An intermediate region 44 is disposed between the first end region 40 and the second end region 48.

As shown, the feminine pad 10 comprises a generally elongated oval shape. However, any suitable shape may be utilized. Some examples include hourglass, offset hourglass (one end is wider than an opposite end and a narrowed mid-section between the ends), etc. The feminine pad 10 may be symmetric about the longitudinal axis 80 or asymmetric about the longitudinal axis 80. Similarly, the feminine pad 10 may be symmetric about the lateral axis 90 or asymmetric about the lateral axis 90.

Figure 2A:
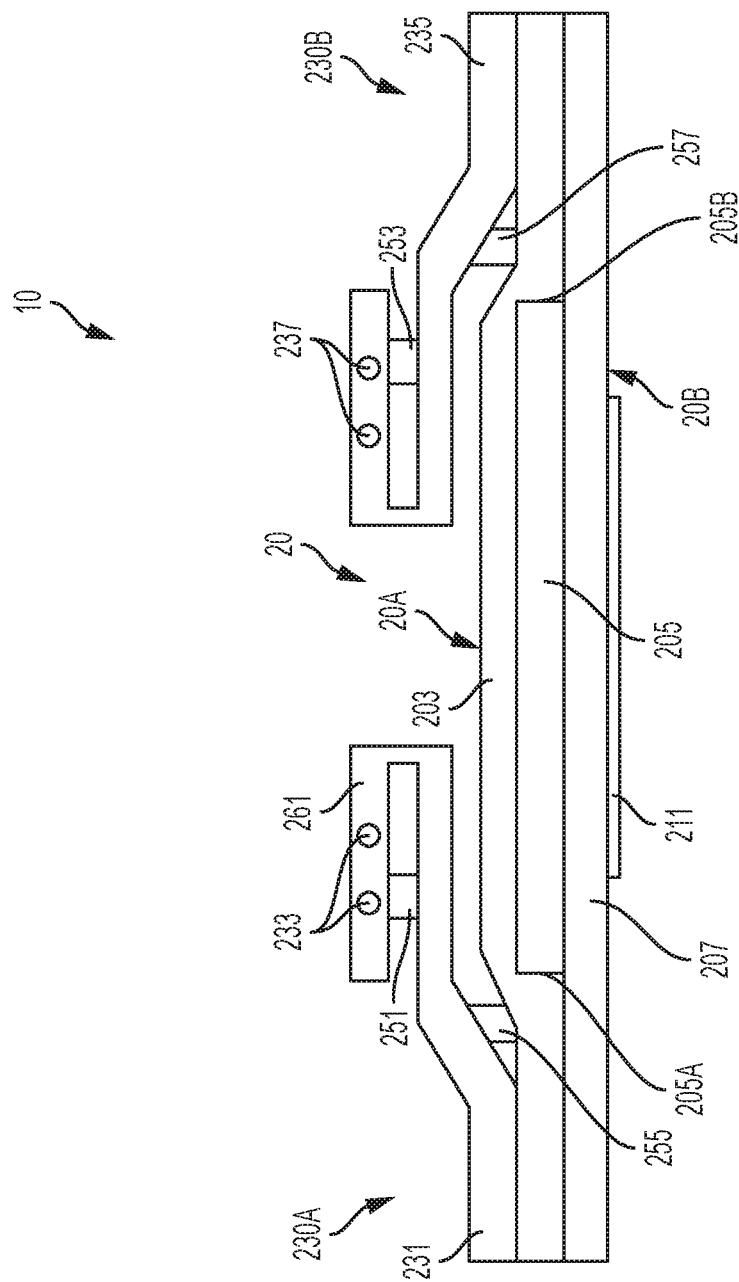
FIG. 2A is a cross sectional view of the feminine pad of FIG. 1 taken along line 2-2.

Regarding FIG. 2A, the chassis 20 may further comprises a topsheet 203, a backsheet 207, and an absorbent structure 205 positioned between the topsheet 203 and the backsheet 207. Additional layers are contemplated between the topsheet 203 and the backsheet 207. Some examples include secondary topsheets, acquisition layers, distribution layers, etc. The chassis 20 further comprises a wearer-facing surface 20A and a garment-facing surface 20B. The wearer-facing surface 20A may comprise the topsheet 203, and the garment-facing surface 20B may comprise the backsheet.

The feminine pad 10 may further comprise a first barrier cuff 230A and a second barrier cuff 230B and fastening adhesive 211 disposed on the garment-facing surface 20B of the chassis 20. As shown, the fastening adhesive 211 may not extend out laterally to the same extent as the absorbent core 205. As such, placement of the fastening adhesive 211 may not be able to provide much help in the way of holding down corners 26A, 26B, 28A, 28B (See FIG. 1) of the feminine pad 10. As such, constructions where pad curl is reduced would be beneficial.

The first barrier cuff 230A and the second barrier cuff 230B may be attached to the chassis 20 in any suitable location. For example, as shown, the first barrier cuff 230A and the second barrier cuff 230B may be attached to a wearer-facing surface 20A of the chassis 20. As shown, the first barrier cuff 230A and the second barrier cuff 230B are attached to the topsheet 203. In some forms, the first barrier cuff 230A and the second barrier cuff 230B may be attached to a garment-facing surface 20B of the chassis 20. For example, the first barrier cuff 230A and the second barrier cuff 230B may be attached to the backsheet 207. Some examples of other suitable barrier cuffs are described in U.S. Pat. Nos. 4,695,278; 4,704,115; 4,795,454; 4,909,803; U.S. Patent Application Publication No. 2009/0312730.

As shown, in some forms, the first barrier cuff 230A comprises a first cover 231 and a first elastic member 233. The second barrier cuff 230B comprises a second cover 235 and a second elastic member 237. As shown, the first cover 231 may fully enclose the first elastic member 233. Similarly, the second cover 235 may fully enclose the second elastic member 237.

While the first barrier cuff 230A and the second barrier cuff 230B are shown as discrete elements which are attached to the chassis 20, any suitable configuration may be utilized. For example, the first cover 231 and/or the second cover 235 may comprise a portion of the topsheet 203 and/or a portion of the backsheet 207. In such forms, the first barrier cuff 230A and/or the second barrier cuff 230B may be integrally formed with the chassis 20. A form where the first barrier cuff 230A and the second barrier cuff 230B are integrally formed with the chassis 20 is shown in FIG. 2B and discussed hereafter.

Figure 2B:
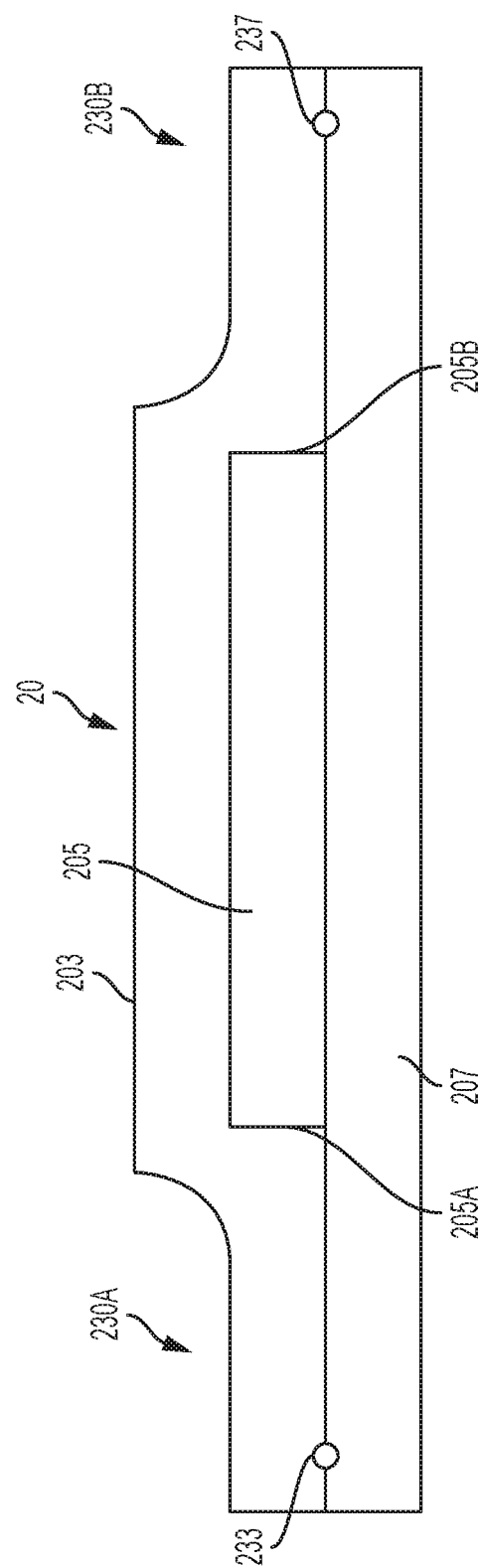
FIG. 2B is a cross-sectional view of an alternate form of a feminine pad constructed in accordance with the present invention.

Referring to FIGS. 2A and 2B, the first elastic member 233 and the second elastic member 237 may be attached to the first cover 231 and the second cover 235, respectively, by any suitable means. In one example, the first elastic member may be adhesively attached to the first cover 231. Similarly, the second elastic member 237 may be adhesively attached to the second cover 235. For example, as shown, first adhesive portions 251 and 253 may attach the elastic members 233 and 237 to their respective covers 231 and 235. Similarly, second adhesive portions 255 and 257 may attach their respective covers 231 and 235 to the topsheet 203. As described below, the first elastic member 233 and the second elastic member 237 may be attached in only a portion the first cover 231 and second cover 235, respectively. Additional forms are contemplated where the first elastic member 233 and/or the second elastic member 237 are attached to the chassis 20 in conjunction with or independently from their respective covers 231 and 235.

Referring back to FIGS. 1 and 2A, the elastic members 233 and 237 may be disposed laterally inboard of side edges 205A and 205B of the absorbent core 205. In other forms, the elastic members 233 and 237 may be disposed laterally outboard of the side edges 205A and 205B of the absorbent core 205. Still in other forms, the elastic members 233 and 237 may be disposed laterally inboard of the side edges 205A and 205B of the absorbent core 205 in the first end region 40 and the second end region 48 but laterally outboard of side edges 205A and 205B of the absorbent core 205 in the intermediate region 44. Additional forms are contemplated where the elastic members 233 and 237 are disposed laterally inboard of the side edges 205A and 205B of the absorbent core 205 in the first end region 40 but are disposed outboard of the side edges 205A and 205B of the absorbent core 205 in the intermediate region 44 and/or the second end region 48.

Referring back to FIG. 2B, and as discussed previously, the first barrier cuff 230A and the second barrier cuff 230B may comprise a portion of the topsheet 203 and the backsheet 207. The first elastic member 233 and the second elastic member 235 may be attached only to a portion of the topsheet 203 and backsheet 205. In other forms, the first elastic member 233 and the second elastic member 235 may be attached to the topsheet 203 and backsheet 205 at their respective ends as described hereafter. As shown, the elastic members 233 and 237 may be disposed laterally outboard of the side edges 205A and 205B of the absorbent core 205.

The elastic members comprised by the barrier cuffs can be glued in, in various glue lengths using various glues and glue amounts and placements. Placement of the glue is yet another variable which should be considered especially when designed with the core flexibility in mind. Gluing of the elastic members and the covers create anchor points on the pad. The locations of the anchor points are important. For example, anchor points outboard of the side edges 205A and 205B of the absorbent core 205 can mitigate the forces applied to the absorbent core 205; however, anchor points disposed too far outboard of the side edges 205A and 205B of the absorbent core 205 can increase the amount of curl on the end edges 26 and 28. Anchor points disposed too far inboard of the side edges 205A and 205B of the absorbent core 205 can negatively impact the performance of the barrier cuffs 230A and 230B. This can be particularly important on cores with contoured shapes as wider ends coupled with a narrower crotch region can create artificial bending points for which elastomeric forces can act to deform the shape of the pad.

In some forms, adhesive may be applied to the covers in a discontinuous manner. For example, adhesive applied to the cover in the intermediate region 44 may be disposed outboard of the side edges 205A and 205B of the absorbent core 205. However, in the end regions 40 and 48, adhesive may be applied to the covers more proximal to the side edges 205A and 205B of the absorbent core 205. Such application of adhesive urges the barrier cuff inward and can help to create a more effective gasket. Adhesive patterns for barrier cuffs are discussed in depth in U.S. Patent Application Publication No. 2011/0319855.

Minimum spacing between the first barrier cuff 230A and the second barrier cuff 230B may be largely driven by female anatomy. However, as discussed previously, tradeoffs can occur where the barrier cuffs (and their respective elastic members) are disposed too far outboard of the absorbent core 205 and too far inboard of the absorbent core 205. As such, spacing between the most distal elastic members of their respective barrier cuffs should be carefully selected. Starting from the narrowest width, spacing between the most distal elastic members of the first barrier cuff 230A and the second barrier cuff 230B should be large enough to allow sufficient access to the absorbent core 205 during use while also taking into account the forces which will be applied to the pad. If too narrow, access to a portion of the absorbent core 205 could be obstructed which could lead to leakage despite the barrier cuffs 230A and 230B. In some forms of the present invention, minimum spacing between the elastic member of the first barrier cuff 230A and the elastic member of the second barrier cuff 230B which are most distal to one another may be at least 20 mm. Any suitable spacing may be utilized. For example, in some forms of the present invention, the spacing may be greater than or equal to about 20 mm, greater than about 30 mm, greater than about 33 mm, greater than about 35 mm, greater than about 40 mm, greater than about 45 mm, greater than about 50 mm, greater than about 54 mm, greater than about 60 mm, greater than about 65 mm, less than or equal to about 70 mm, or less than about 65 mm, or less than about 60 mm, less than about 55 mm, less than about 50 mm, less than about 45 mm, less than about 40 mm, less than about 35 mm, less than about 30 mm, less than about 25 mm, specifically including any values within these ranges or any ranges created thereby.

Figure 5:
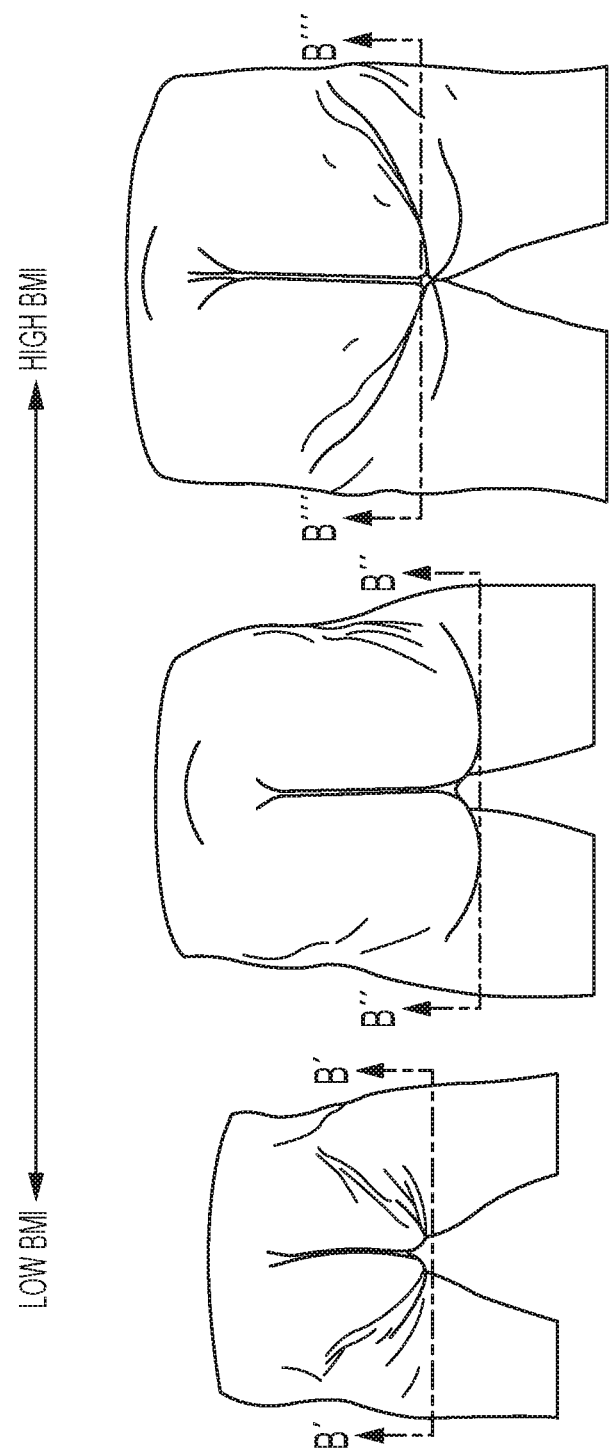
FIG. 5 shows representative female body shapes of differing BMI where the transverse plane B:B is determined at the gluteal sulcus.
Figure 6:
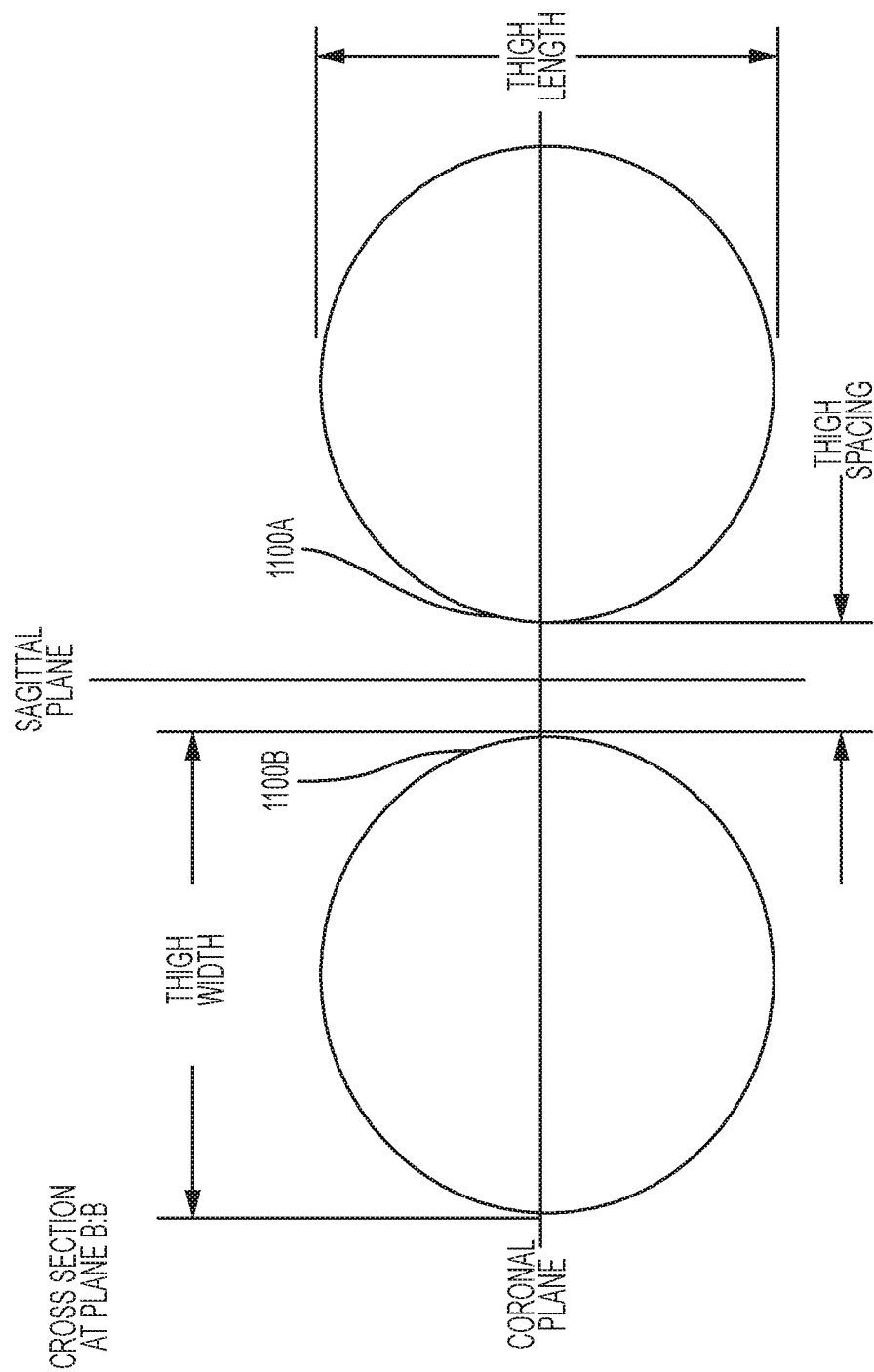
FIG. 6 shows representative female morphological measurements taken at plane B:B of FIG. 5, including thigh spacing, thigh diameter parallel to the sagittal plane (thigh length), and thigh diameter parallel to the coronal plane (thigh width).

The above spacing can be critical in ensuring that the barrier cuffs 230A and 230B contact the body of the user in an appropriate location. To gain an understanding of an appropriate location, it is pertinent to mention a few reference points of user anatomy. A "coronal plane" as used herein, describes a vertical plane which extends through a standing female body dividing said body into anterior and posterior portions, and said coronal plane extending through the shoulder and vaginal opening, bisecting vaginal opening into anterior and posterior portions. A "sagittal plane" as used herein describes a plane which extends through the body of a standing wearer and bisects the body of the standing wearer into left and right halves. "Thigh Spacing" means the narrowest lateral distance between the thighs—inner portions of the thigh 1100A and 1100B (see FIG. 6)—while the person whose thighs are being measured is in the neutral position with their feet approximately shoulder width apart. The lateral distance being parallel to the coronal plane and being on a transverse plane. The transverse plane being perpendicular to the coronal plane and extending through the Gluteal Sulcus (the gluteal sulcus is often referred to as the fold of the buttock or the gluteal fold of the horizontal gluteal crease). This is illustrated in FIG. 5 and in FIG. 6 at plane B:B of FIG. 5.

Figure 7B:
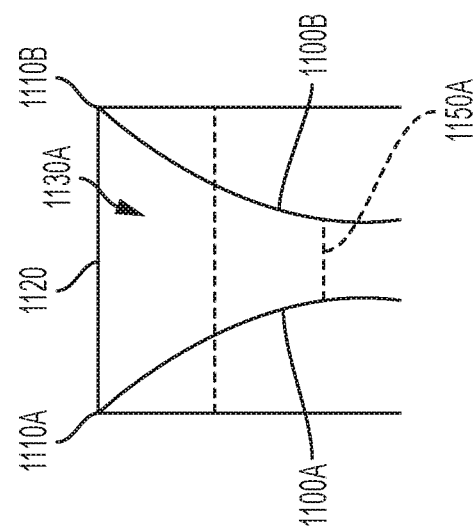
FIG. 7B shows an approximation of the open area of the crotch on the coronal plane defined at the location where inner thighs intersect the torso and the gluteal sulcus for a low BMI value, e.g. 15.
Figure 7A:
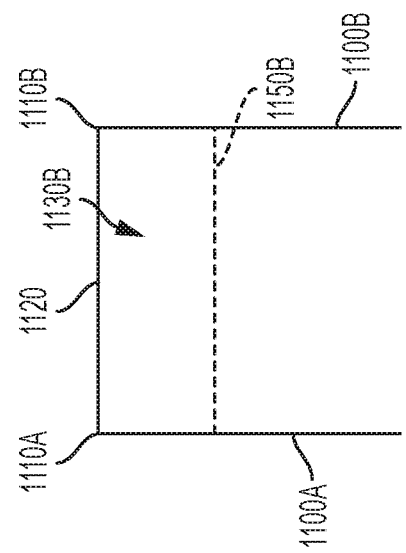
FIG. 7A shows an approximation of the open area of the crotch on the coronal plane, defined at the location where inner thighs 1100A and 1100B intersect the torso 1120 and the gluteal sulcus for a high BMI value, e.g. 35.

FIG. 7A depicts an approximated area 1130A on the coronal plane when viewing the coronal plane from the anterior portion into the posterior portion of the body. The approximated area 1130A shown is that for a high BMI wearer, e.g. 35. The area 1130A is defined by an intersection 1110A between a body torso 1120 and an inner thigh 1100A, an intersection 1100B between the body torso 1120 and an inner thigh 1100B and a transverse plane 1150A extending through the gluteal sulcus. As depicted, the area 1130A may be approximated by an inverted trapezoid. As BMI decreases, angles at the intersections 1110A and 1110B increase. In FIG. 7B, an approximated area 1130B for a lower BMI wearer, e.g. 15, is depicted. As shown, a transverse plane 1150B extending through the gluteal sulcus is much closer to the torso 1120 than of FIG. 7A. The transverse planes 1150A and 1150B represent relative spacing of the panty to the torso. As depicted, the transverse plane 1150B is much closer to the torso 1120 than the transverse plane 1150A.

Barrier cuffs of the present invention may engage a user at the intersections 1110A and 1110B between the inner thigh 1100A and torso 1120 and the inner thigh 1100B and torso 1120. Barrier cuffs which are spaced laterally inward from the intersections 1110A and 110B can increase the likelihood of leakage. For example, when one or more barrier cuffs engage the torso 1120 laterally inboard of the intersections 1110A and/or 1110B, the one or more barrier cuffs may divert the path of fluids from the vaginal opening such that these fluids travel along an outside surface of the barrier cuff rather than to the topsheet of the pad. In contrast, barrier cuffs which engage the inner thigh 1100A and 1100B rather than the intersections 1110A and 1110B, can have decreased efficacy. For example, the barrier cuffs may tend drag along the inner thigh 1100A and 1100B when donning the pad such that in the final orientation, the barrier cuffs are sloped downward. This downward slope of the barrier cuffs and decrease the efficacy of the barrier cuffs. The above ranges for spacing of the barrier cuffs, were empirically determined based upon clinical measurement of crotch width at the torso 1120 and extrapolation of the results therefrom.

Yet another factor is folds of the pad. Pads generally contain one or more folds in order to make the pad more consumer friendly and easy to transport and store. Additionally, folding the pad can reduce the likelihood of elastic creep during storage. However, these fold lines can act as bending points upon which elastomeric forces can act to deform the shape of the pad. And, similar to the anchor points discussed above, anchor points disposed too far beyond a fold line can be problematic. Anchor points disposed too far beyond a fold line can increase the torque lever arm acting on the pad in the MD direction causing pad curl and/or the pad to fold back into the folded state.

Referring back to FIG. 1, feminine pad 10 may further comprise a first fold line 50 and a second fold line 55. The first fold line 50 can define a boundary between the first end region 40 and the intermediate region 44. The second fold line 55 can define a boundary between the second end region 48 and the intermediate region 44. The first end region 40 can be defined by the end edge 26, the first fold line 50, and a portion of the side edges 22 and 24 disposed between the end edge 26 and the first fold line 50. The intermediate area 44 can be by the first fold line 50, the second fold line 55, and a portion of the side edges 22 and 24 disposed between the first fold line 50 and second fold line 55. The second end region 48 is defined by the second fold line 55, end edge 28, and a portion of the side edges 22 and 24 disposed between the end edge 28 and the second fold line 55. The fold lines 50 and 55 can be parallel and can be co-linear (on average) with the folds which are created via the packaging process for the feminine pad 10.

In some forms, the first fold line 50 and second fold line 55, may be configured such that the fold lines 50 and 55 dissect the pad into thirds. In other forms, the first fold line 50 may be offset toward the end edge 28, and the second fold line 55 may be offset toward the end edge 28. In such forms, this can allow the second end region 48 to be tucked between the intermediate region 44 and the first end region 40 when the pad is in the folded configuration. Still in other forms, the first fold line 50 may be offset toward the end edge 26, and the second fold line 55 may be offset toward the end edge 26. In such forms, this can allow the first end region 40 to be tucked between the intermediate region 44 and the second end region 48 when the pad is in the folded configuration. In some forms of the present invention, the offset either toward the end edge 26 or the end edge 28 may be greater than about 5 mm, greater than about 10 mm, greater than about 15 mm, greater than about 20 mm, greater than about 25 mm, specifically including any values within these ranges and any ranges formed thereby.

Figure 3A:
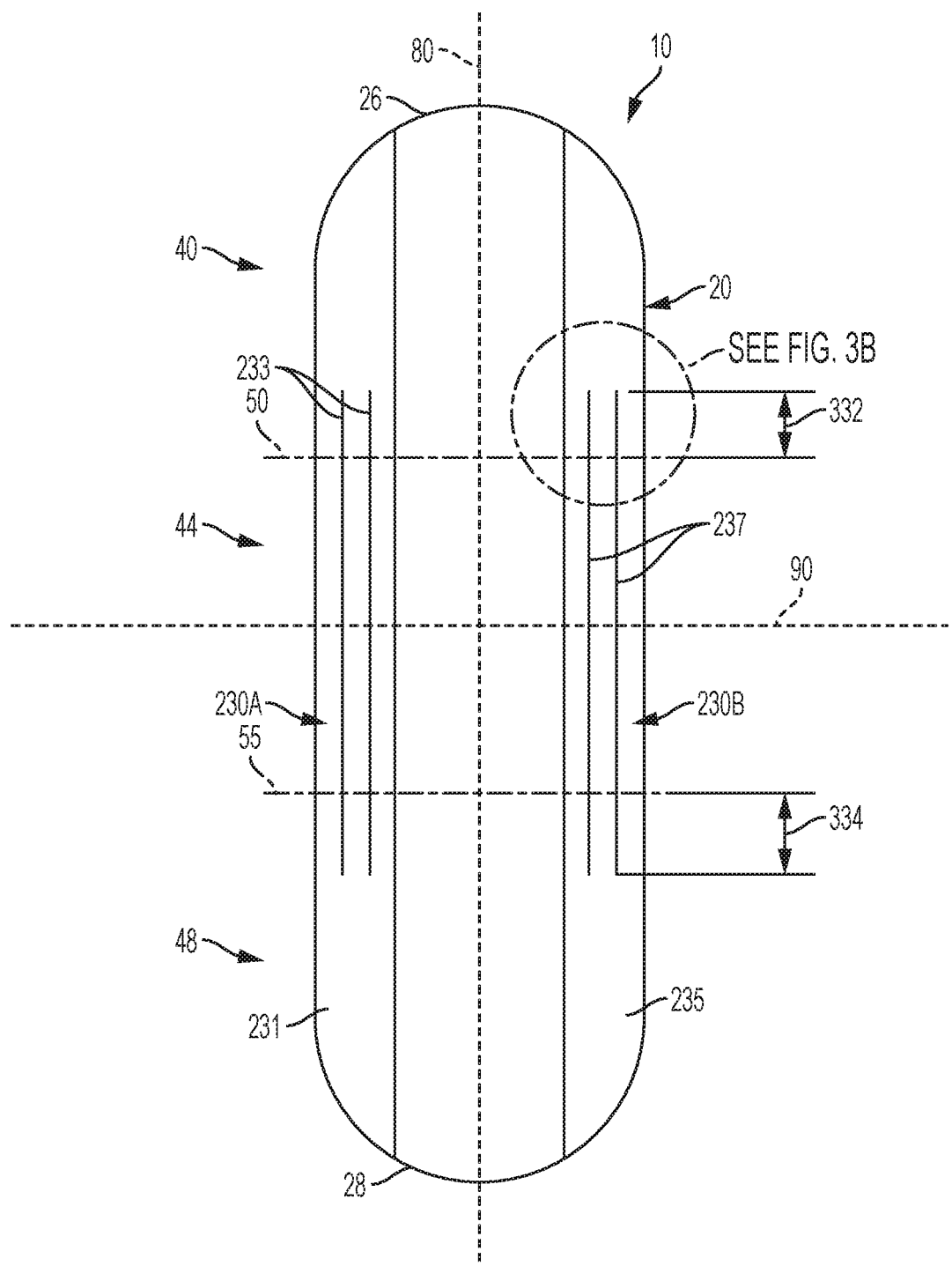
FIG. 3A is plan view showing the feminine pad of FIG. 1 showing the additional feature of barrier cuffs.

Referring to FIG. 3A, the first barrier cuff 230A may extend from one end edge 26 to the other end edge 28, and the second barrier cuff 230B may extend from one end edge 26 to the other end edge 28. Similarly, the first cover 231 and the second cover 235 may extend from one end edge 26 to the other end edge 28. As shown, the first elastic member 233 and the second elastic member 237 may be attached to their respective covers inboard of the end edges 26 and 28. For example, the first elastic member 233 may be attached to the first cover 231 in a first attachment zone 332 and a second attachment zone 334. In some forms, the first attachment zone 332 extends from the first fold line 50 into the first end region 40 by not more than 30 mm. Similarly, in some embodiments, the second attachment zone 334 extends from the second fold line 55 into the second end region 48 by not more than 30 mm. For those forms where the first barrier cuff 230A and the second barrier cuff 230B comprise a portion of the topsheet 203 and the backsheet 207, the first barrier cuff 230A and second barrier cuff 230B may be configured as disclosed above.

Figure 3B:
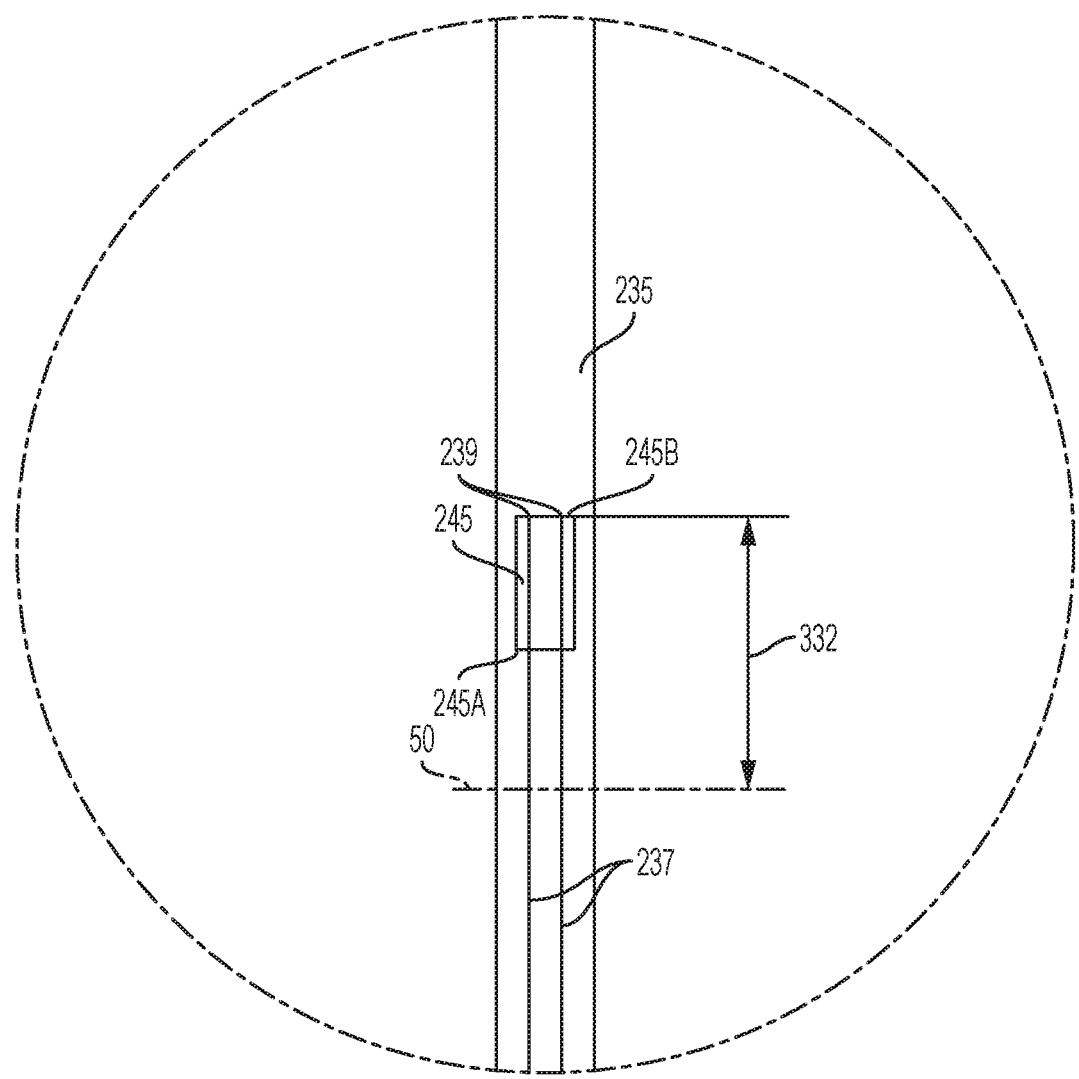
FIG. 3B is a close up view of the elastic member of one of the barrier cuffs of the feminine pad of FIG. 3A.
Figure 3C:
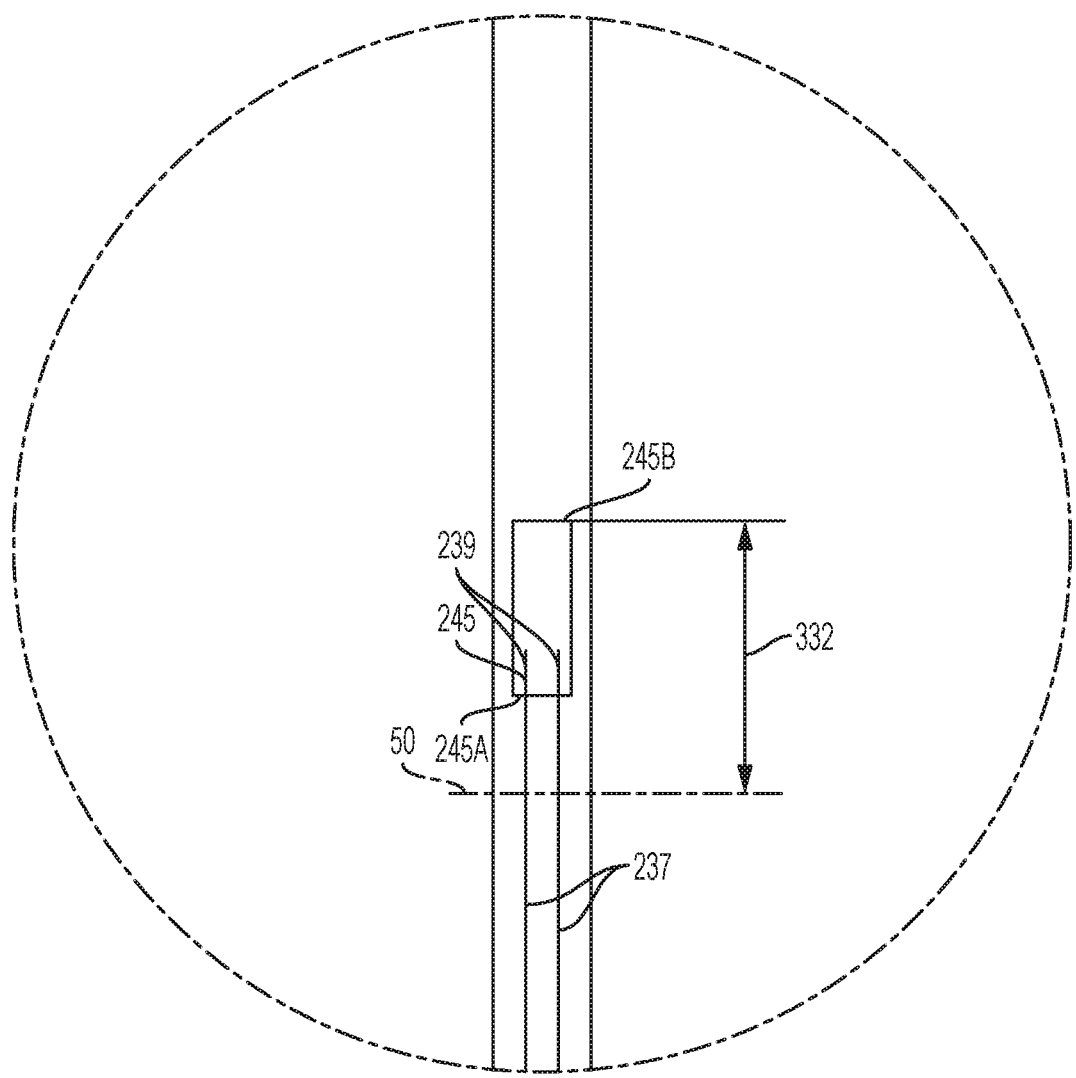
FIG. 3C is a close up view of another configuration of the elastic members of the barrier cuffs for the feminine pads described herein.
Figure 3D:
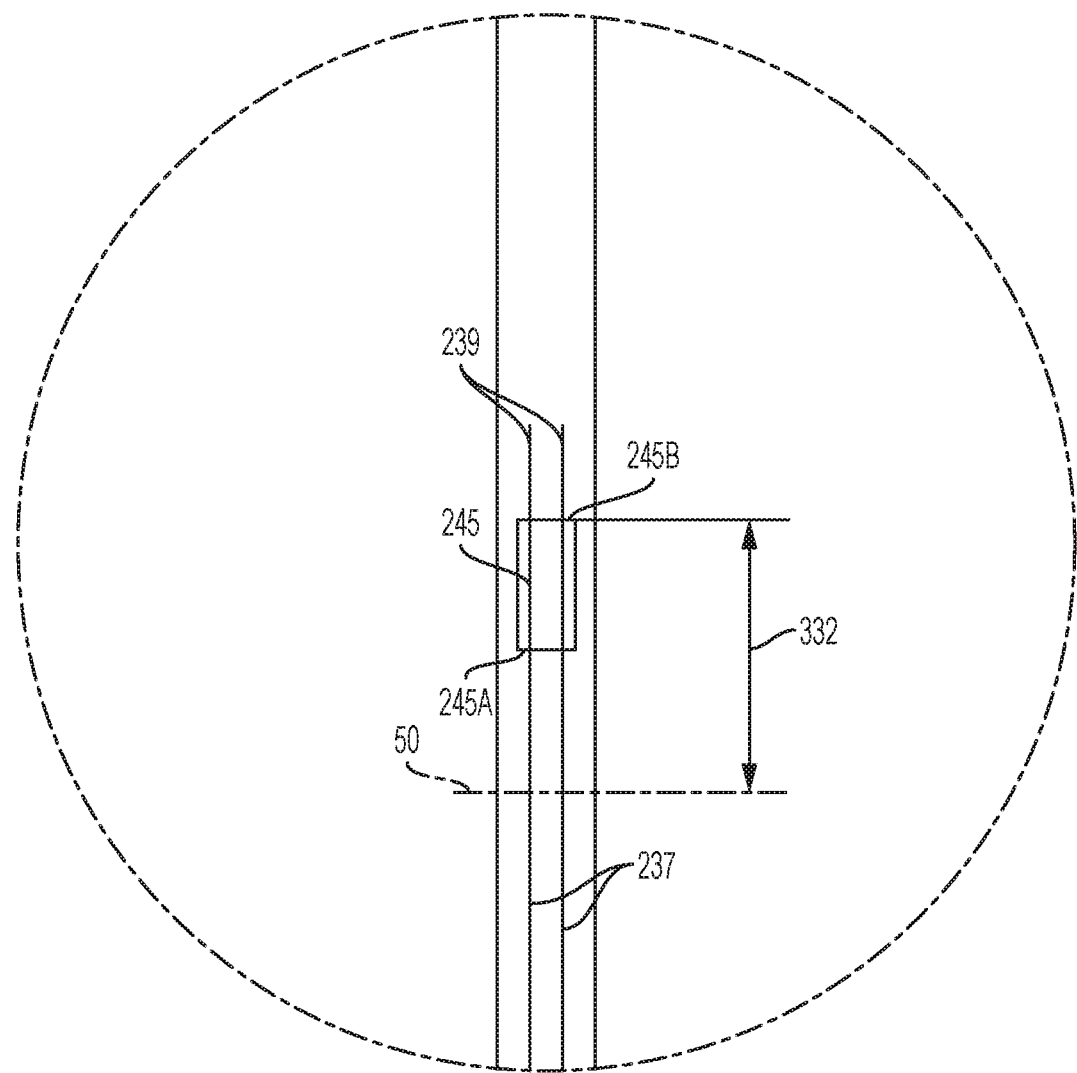
FIG. 3D is a close up view of another configuration of the elastic members of the barrier cuffs for the feminine pads described herein.
Figure 4:
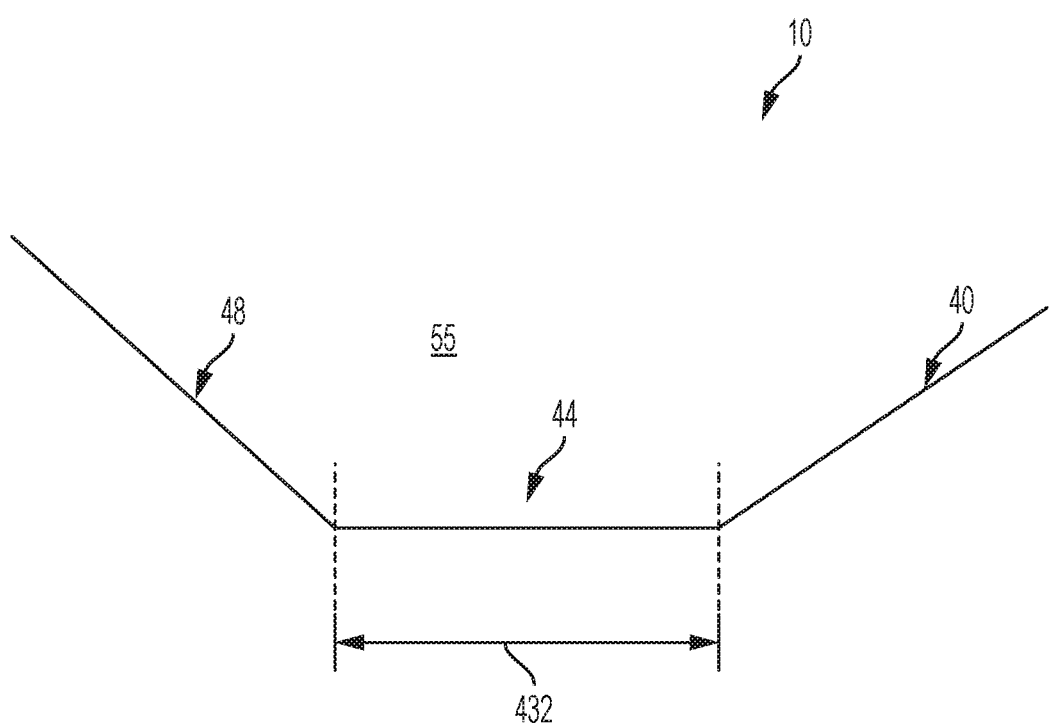
FIG. 4 is a schematic side view showing a feminine pad and exemplary fold lines.

The first attachment zone 332 and the second attachment zone 334 may be bounded by their respective fold lines, e.g. the first fold line 50 for the first attachment zone 332 and the second fold line 55 for the second attachment zone 334. And where adhesive is utilized to join the elastic members 233 and 237 to their covers, the first attachment zone 332 and the second attachment zone 334 may be bounded by a leading edge 245A (shown in FIG. 3B) of the adhesive portion 245 which joins the elastic member to its respective cover. Referring to FIG. 3B, ends 239 of the second elastic member 237 may be coterminous with a boundary of the first attachment zone 332. Specifically, adhesive 245 has the inboard edge 245A and an outboard edge 245B, wherein the outboard edge 245B is coterminous with ends 239 of the second elastic member 237. However, ends 239 of the second elastic member 237 may be non-coterminous with the outboard edge 245B of the adhesive portion 245. For example, as shown in FIG. 3C, adhesive 245 may be applied to the ends 239 of the second elastic member 237 and such adhesive 245 may extend longitudinally beyond the ends 239 of the second elastic member 237. As another example, referring to FIG. 3D, the ends 239 of the second elastic member 237 may extend beyond the adhesive 245 which secures the second elastic member 237 to its respective cover.

As stated previously, in some forms of the present invention, the first elastic member 233 may be attached to the chassis 20 directly either in conjunction with or independently from the attachment to the first cover 231. In such embodiments, the above regarding attachment zones may similarly apply. Namely, the first attachment zone 332 may extend from the first fold line 50 into the first end region 40 by not more than 20 mm. Similarly, the second attachment zone 334 may extend from the second fold line 55 into the second end region 48 by not more than 20 mm. It is believed that the limit of extension of the first attachment area 332 and the second attachment area 334 beyond the first fold line 50 and the second fold line 55, respectively, reduces the potential moment arm which urges the first end region 40 and/or the second end region 48 into the folded position. The second elastic member 237 may be similarly configured to the first elastic member 233 with regard to the first attachment zone 332 and the second attachment zone 334. And for those forms where the first barrier cuff and second barrier cuff comprise a portion of the topsheet and the backsheet, the first elastic member and second elastic member may be similarly configured to those forms disclosed above.

Referring to FIG. 3A, in some forms of the present invention, the first elastic member 233 and the second elastic member 237 are attached to their respective covers 231 and 235 continuously in the intermediate region 44. In other forms of the present invention, the first elastic member 233 and the second elastic member 237 may be unattached to their respective covers 231 and 235 in the intermediate region 44. In some forms of the present invention, the first elastic member 233 and/or the second elastic member 237 may be attached to their respective covers 231/235 and/or the chassis 20 intermittently. For example, the first elastic member 233 may be attached to the first cover 231 in the intermediate region 44 less than about 90 percent of a distance between the first fold line 50 and the second fold line 55. In some forms of the present invention, the first elastic member 233 may be attached to the first cover 231 in the intermediate region 44 less than about 80 percent, less than about 70 percent, less than about 60 percent, less than about 50 percent, less than about 40 percent, less than about 30 percent, less than about 20 percent of the distance between the first fold line 50 and the second fold line 55, specifically including all numbers within these values and any and all ranges included by or within these values. The second elastic member 237 may be similarly configured. And for those forms where the first barrier cuff and second barrier cuff comprise a portion of the topsheet and the backsheet, the first elastic member and second elastic member may be similarly configured to those forms described above.

The problems associated with barrier cuff elastics as described heretofore are similarly applicable for those feminine pads which comprise a single fold or comprise no folds. For example, for those feminine pads comprising only one fold, the fold line may be considered to bisect the pad into halves. However, for the purposes of determining the appropriate attachment zone of the elastic members to the chassis or to their respective covers, fold lines may be approximated which dissect the length of the pad into thirds. Similarly, for those feminine pads which are packaged in a flat position, imaginary fold lines dissect the feminine pad into thirds. For those feminine pads comprising more than two folds—where the folds are generally parallel to the lateral axis of the pad—the fold lines are co-linear (on average) with the folds which are created via packaging. In such forms, the fold lines which are most proximate to the end regions of the pad are to be considered. For those pads of the present invention which do comprise folds, the boundary lines associated therewith may be offset as described above.

As noted previously, a stiffer article may resist the barrier cuff forces to a larger extent than a less stiff article. However, stiffer articles typically are not seen as wearer friendly as they can provide a harsh feel to the wearer and generally do not conform well to the body of the user. Examples of conventional articles and articles constructed in accordance with the present invention are provided hereafter.

Similarly, elastic members having a lower spring value can be utilized. However, reduction of the spring value of the elastic members can negatively impact the functionality of the barrier cuffs. For example, elastic members having too low of a spring value can decrease the barrier cuff height in use. The decreased height can increase the likelihood of leakage beyond the barrier cuff.

Referring back to FIGS. 2A and 2B, the feminine pad 10 of the present invention may utilize any suitable topsheet 203, any suitable backsheet 207, and any suitable absorbent core 205. As shown, the topsheet 203 and the backsheet 207 may have length and width dimensions generally larger than those of the absorbent core 205. In some forms of the present invention, the topsheet 203 and the backsheet 207 extend beyond the edges of the absorbent core 205 to thereby form the periphery of the feminine pad 10. The topsheet 203, the backsheet 207, and the absorbent core 205 may be assembled in a variety of well-known configurations known to those of skill in the art.

The absorbent core 205 of the present invention may comprise any suitable shape. For example, in some forms of the present invention, the absorbent core 205 may comprise a contoured shape, e.g. narrower in the intermediate region than in the end regions. As another example, the absorbent core 205 may comprise a rectangular shape. As yet another example, the absorbent core may comprise a tapered shape having a wider portion in one end region of the pad which tapers to a narrower end region in the other end region of the pad. The absorbent core 205 may comprise varying stiffness in the MD and CD.

The absorbent core 205 may comprise any absorbent member which is generally compressible, conformable, non-irritating to the wearer's skin, and capable of absorbing and retaining liquids such as urine and other certain body exudates including menses. The absorbent core 205 may be manufactured in a wide variety of sizes and shapes (e.g., rectangular, hourglass, asymmetric, etc.) and from a wide variety of liquid-absorbent materials commonly used in disposable feminine articles and other absorbent articles such as comminuted wood pulp which is generally referred to as airfelt. The absorbent core 205 may comprise super-absorbent polymers (SAP) and less than 15%, less than 10%, less than 5%, less than 3%, or less than 1% of airfelt, or be completely free of airfelt. Examples of other suitable absorbent materials comprise creped cellulose wadding, melt-blown polymers including coform, chemically stiffened, modified or cross-linked cellulosic fibers, tissue including tissue wraps and tissue laminates, absorbent foams, absorbent sponges, superabsorbent polymers ("SAP"), e.g. absorbent gelling materials ("AGM"), or any equivalent material or combinations of materials.

The configuration and construction of the absorbent core 205 may vary (e.g., the absorbent structure 205 may have varying caliper zones, a hydrophilic gradient, a superabsorbent gradient, or lower average density and lower average basis weight acquisition zones; or may comprise one or more layers or structures). Further, the size and absorbent capacity of the absorbent core 205 may also be varied to accommodate a variety of wearers. However, the total absorbent capacity of the absorbent core 205 should be compatible with the design loading and the intended use of the feminine pad 10.

In certain forms of the present invention, the absorbent core 205 can be relatively thin, such as, for example, less than about 10 mm, or less than about 5 mm in thickness, or less than about 3 mm, or less than about 1 mm in thickness. Thickness can be measured by any means known in the art for doing so while the core is under a uniform pressure of 0.25 psi. In some exemplary forms of the present invention, the absorbent core 205 can comprise absorbent gelling materials (AGM), including AGM fibers, as is known in the art.

In some forms of the present invention, the absorbent core 205 may comprise a plurality of multi-functional layers. For example, the absorbent core 205 may comprise a core wrap (i.e., the layers enclosing the absorbent material of the absorbent structure 205). The core wrap may be formed by two nonwoven materials, substrates, laminates, films, or other materials. In a form, the core wrap may only comprise a single material, substrate, laminate, or other material wrapped at least partially around itself. Additional layers contemplated are acquisition/distribution layers which are well known in the art.

The absorbent core 205 of the present disclosure may comprise one or more adhesives, for example, to help immobilize the SAP or other absorbent materials within the core wrap and/or to ensure integrity of the core wrap, in particular when the core wrap is made of two or more substrates. The core wrap may extend to a larger area than required for containing the absorbent material(s) within.

Absorbent structures comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., and WO 2012/052172 to Van Malderen.

The absorbent material may comprise one or more continuous layers present within the core wrap with channels having no, or little (e.g., 0.1%-10%) absorbent material positioned therein. In other forms, the absorbent material may be formed as individual pockets or stripes within the core wrap. In the first case, the absorbent material may be, for example, obtained by the application of the continuous layer(s) of absorbent material, with the exception of the absorbent material free, or substantially free, channels. The continuous layer(s) of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 to Hundorf et al., for example.

The absorbent structure 205 may comprise a first absorbent layer and at least a second absorbent layer. The first absorbent layer may comprise a first material and a first layer of absorbent material, which may be 100% or less of SAP, such as 85% to 100% SAP, 90% to 100% SAP, or even 95% to 100% SAP, specifically including all 0.5% increments within the specified ranges and all ranges formed therein or thereby. The second absorbent layer may comprise a second material and a second layer of absorbent material, which may also be 100% or less of SAP (including the ranges specified above). Alternatively, the second absorbent layer may comprise a combination of cellulose, comminuted wood pulp, or the like in combination with SAP. The absorbent core 205 may also comprise a fibrous thermoplastic adhesive material at least partially bonding each layer of the absorbent material to its respective material.

The absorbent core 205 may comprise one or more pockets. The one or more pockets may be provided in addition to the one or more channels or instead of the one or more channels. The pockets may be areas in the absorbent structure that are free of, or substantially free of absorbent material, such as SAP (including the ranges specified above). Other forms and more details regarding channels and pockets that are free of, or substantially free of absorbent materials, such as SAP, within absorbent cores are discussed in greater detail in U.S. Patent Application Publication Nos. 2014/0163500, 2014/0163506, and 2014/0163511, all published on Jun. 12, 2014.

Example absorbent structures for use as the absorbent core 205 of the present disclosure that have achieved wide acceptance described in U.S. Pat. No. 4,610,678, entitled "High-Density Absorbent Structures" issued to Weisman et al., on Sep. 9, 1986; U.S. Pat. No. 4,673,402, entitled "Absorbent Articles With Dual-Layered Cores", issued to Weisman et al., on Jun. 16, 1987; U.S. Pat. No. 4,888,231, entitled "Absorbent Core Having A Dusting Layer", issued to Angstadt on Dec. 19, 1989; and U.S. Pat. No. 4,834,735, entitled "High Density Absorbent Members Having Lower Density and Lower Basis Weight Acquisition Zones", issued to Alemany et al., on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345 entitled "High Efficiency Absorbent Articles For Incontinence Management", issued to Young et al. on Sep. 15, 1992.

The absorbent structure may be a heterogeneous mass comprising enrobeable elements and one or more portions of foam pieces. The discrete portions of foam pieces are open-celled foam. The enrobeable elements may be a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof. The foam may be a High Internal Phase Emulsion (HIPE) foam. Exemplary enrobeable elements and foams are described in greater detail below.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass may have void space found between the enrobeable elements, between the enrobeable elements and the enrobed elements, and between enrobed elements. The void space may contain a gas such as air. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the, such as for example, between 20 g/g and 190 g/g of the heterogeneous mass, such as, for example 30 g/g, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

A discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

A discrete open-cell foam piece may be immobilized such that the discrete open-cell foam piece does not change location within the heterogeneous mass during use of the absorbent structure.

A plurality of discrete open-cell foams may be immobilized such that the discrete open-cell foam pieces do not change location within the heterogeneous mass during use of the absorbent structure.

One or more discrete foam pieces may be immobilized within the heterogeneous mass such that the one or more discrete foam pieces do not change location after being spun at 300 rotations per minute for 30 seconds.

The open-cell foam pieces may be discrete. Open-cell foam pieces are considered discrete in that they are not continuous throughout the entire heterogeneous mass. Not continuous throughout the entire heterogeneous mass represents that at any given point in the heterogeneous mass, the open-cell absorbent foam is not continuous in at least one of the cross sections of a longitudinal, a vertical, and a lateral plane of the heterogeneous mass. The absorbent foam may or may not be continuous in the lateral and the vertical planes of the cross section for a given point in the heterogeneous mass. The absorbent foam may or may not be continuous in the longitudinal and the vertical planes of the cross section for a given point in the heterogeneous mass. The absorbent foam may or may not be continuous in the longitudinal and the lateral planes of the cross section for a given point in the heterogeneous mass.

When the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. A foam piece may be surrounded by the elements that make up the enrobeable elements. A foam piece may be located on the outer perimeter of the heterogeneous mass such that only a portion of the foam piece is entangled with the elements of the heterogeneous mass.

The open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. The open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces. The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

Dependent upon the desired foam density, polymer composition, specific surface area, or pore-size (also referred to as cell size), the open-celled foam may be made with different chemical composition, physical properties, or both. For instance, dependent upon the chemical composition, an open-celled foam may have a density of 0.0010 g/cc to about 0.25 g/cc, or from 0.002 g/cc to about 0.2 g/cc, or from about 0.005 g/cc to about 0.15 g/cc, or from about 0.01 g/cc to about 0.1 g/cc, or from about 0.02 g/cc to about 0.08 g/cc, or about 0.04 g/cc.

Open-cell foam pore-sizes may range in average diameter of from 1 to 800 µm, such as, for example, between 50 and 700 µm, between 100 and 600 µm, between 200 and 500 µm, between 300 and 400 µm.

The foam pieces may have a relatively uniform cell size. For example, the average cell size on one major surface may be about the same or vary by no greater than 10% as compared to the opposing major surface. The average cell size of one major surface of the foam may differ from the opposing surface. For example, in the foaming of a thermosetting material it is not uncommon for a portion of the cells at the bottom of the cell structure to collapse resulting in a lower average cell size on one surface. The cell size may be determined based upon the method found below.

The foams preferably are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 µm in average diameter size are in fluid communication with at least one adjoining cell.

In addition to being open-celled, the foams may be sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

For example when used in certain absorbent articles, an open-cell foam may be flexible and exhibit an appropriate glass transition temperature (Tg). The Tg represents the midpoint of the transition between the glassy and rubbery states of the polymer.

The Tg of a region may be less than about 200° C. for foams used at about ambient temperature conditions, or less than about 90° C. The Tg may be less than 50° C.

The open-cell foam pieces may be distributed in any suitable manner throughout the heterogeneous mass. The open-cell foam pieces may be profiled along the vertical axis such that smaller pieces are located above larger pieces. Alternatively, the pieces may be profiled such that smaller pieces are below larger pieces. The open-cell pieces may be profiled along a vertical axis such that they alternate in size along the axis.

The open-cell foam pieces may be profiled along the longitudinal axis such that smaller pieces are located in front of larger pieces. Alternatively, the pieces may be profiled such that smaller pieces are behind larger pieces. The open-cell pieces may be profiled along a longitudinal axis such that they alternate in size along the axis.

The open-cell foam pieces may be profiled along the lateral axis such the size of the pieces goes from small to large or from large to small along the lateral axis. Alternatively, the open-cell pieces may be profiled along a lateral axis such that they alternate in size along the axis.

The open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

The open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. The open-cell foam pieces may be distributed in a manner that forms a design or shape when viewed from a top planar view. The open-cell foam pieces may be distributed in a manner that forms stripes, ellipticals, squares, or any other known shape or pattern.

In an embodiment, the open-cell foam pieces are in the form of stripes. The stripes may be formed during the formation of the heterogeneous mass or by formation means after polymerization. The stripes may run along the longitudinal length of the heterogeneous mass layer, along the lateral length of the heterogeneous mass layer, or a combination of both the longitudinal length and the lateral length. The stripes may be continuous or discontinuous. The stripes may run along a diagonal to either the longitudinal length or the lateral length of the heterogeneous mass layer. The stripes may be separated by canals.

In an embodiment, the open-cell foam forms a grid comprising discontinuous canals. The canals may run along the longitudinal length of the heterogeneous mass layer, along the lateral length of the heterogeneous mass layer, or a combination of both the longitudinal length and the lateral length.

Formation means known for deforming a generally planar fibrous web into a three-dimensional structure are utilized in the present invention to modify as-made absorbent materials into absorbent materials having relatively higher permeability without a significant corresponding decrease in capillary pressure. Formation means may comprise a pair of intermeshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, other known formation technologies, such as creping, necking/consolidation, corrugating, embossing, button break, hot pin punching, and the like are believed to be able to produce absorbent materials having some degree of relatively higher permeability without a significant corresponding decrease in capillary pressure. Formation means utilizing rolls include "ring rolling", a "SELF" or "SELF'ing" process, in which SELF stands for Structural Elastic Like Film, as "micro-SELF", and "rotary knife aperturing" (RKA); as described in U.S. Pat. No. 7,935,207 Zhao et al., granted May 3, 2011.

The distribution may be optimized dependent on the intended use of the heterogeneous mass. For example, a different distribution may be chosen for the absorption of aqueous fluids such as urine when used in a diaper or water when used in a paper towel versus for the absorption of a proteinaceous fluid such as menses. Further, the distribution may be optimized for uses such as dosing an active or to use the foam as a reinforcing element.

Different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

The foam pieces may be similar in composition yet exhibit different properties. For example, using HIPE foam, some foam pieces may be thin until wet while others may have been expanded within the heterogeneous mass.

The foam pieces and enrobeable elements may be selected to complement each other. For example, a foam that exhibits high permeability with low capillarity may enrobe an element that exhibits high capillarity to wick the fluid through the heterogeneous mass. It is understood that other combinations may be possible wherein the foam pieces complement each other or wherein the foam pieces and enrobeable elements both exhibit similar properties.

Profiling may occur using more than one heterogeneous mass with each heterogeneous mass having one or more types of foam pieces. The plurality of heterogeneous masses may be layered so that the foam is profiled along any one of the longitudinal, lateral, or vertical axis based on one or more characteristics of the open-cell foam pieces for an overall product that contains the plurality of heterogeneous masses. Further, each heterogeneous mass may have a different enrobeable element to which the foam is attached. For example, a first heterogeneous mass may have foam particles enrobing a nonwoven while a second heterogeneous mass adjacent the first heterogeneous mass may have foam particles enrobing a film or one surface of a film.

The open-celled foam may be a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. The aqueous phase to oil phase ratio may be between about 10:1 and about 75:1, and the aqueous phase to oil phase ratio may be between about 13:1 and about 65:1. This is termed the "water-to-oil" or W:O ratio and may be used to determine the density of the resulting polyHIPE foam. As discussed, the oil phase may contain one or more of monomers, comonomers, photoinitiators, crosslinkers, and emulsifiers, as well as optional components. The water phase may contain water and one or more components such as electrolyte, initiator, or optional components.

The open-cell foam may be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, or after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE may then be withdrawn or pumped from the mixing zone. One method for forming HIPEs using a continuous process is described in U.S. Pat. No. 5,149,720 (DesMarais et al) issued Sep. 22, 1992; U.S. Pat. No. 5,827,909 (DesMarais) issued Oct. 27, 1998; and U.S. Pat. No. 6,369,121 (Catalfamo et al.) issued Apr. 9, 2002.

The emulsion may be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. Foam pieces may be squeezed free of most of the aqueous phase by using compression, for example by running the heterogeneous mass comprising the foam pieces through one or more pairs of nip rollers. The nip rollers may be positioned such that they squeeze the aqueous phase out of the foam pieces. The nip rollers may be porous and have a vacuum applied from the inside such that they assist in drawing aqueous phase out of the foam pieces. Nip rollers may be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller may be pressurized while the other, for example the second nip roller, may be evacuated, so as to both blow and draw the aqueous phase out the of the foam. The nip rollers may also be heated to assist in removing the aqueous phase. Nip rollers may be applied to non-rigid foams, that is, foams whose walls would not be destroyed by compressing the foam pieces.

In place of or in combination with nip rollers, the aqueous phase may be removed by sending the foam pieces through a drying zone where it is heated, exposed to a vacuum, or a combination of heat and vacuum exposure. Heat may be applied, for example, by running the foam though a forced air oven, IR oven, microwave oven or radiowave oven. The extent to which a foam is dried depends on the application. Greater than 50% of the aqueous phase may be removed. Greater than 90%, and in still other embodiments greater than 95% of the aqueous phase may be removed during the drying process.

Open-cell foam may be produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photoinitiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain embodiments from about 2% to about 8%, to modify properties of the HIPE foams. "Toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers may be used to slow down the polymerization rate of a HIPE. Examples of monomers of this type may have styrene and vinyl chloride.

The oil phase may further contain an emulsifier used for stabilizing the HIPE. Emulsifiers used in a HIPE may include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of—branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of—branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they may have between about 1% and about 20%, in certain embodiments from about 2% to about 15%, and in certain other embodiments from about 3% to about 12% by weight of the oil phase. Coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. Ditallow dimethyl ammonium methyl sulfate (DTDMAMS) may be used as a coemulsifier.

The oil phase may comprise a photoinitiator at between about 0.05% and about 10%, and in certain embodiments between about 0.2% and about 10% by weight of the oil phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of about 200 nanometers (nm) to about 800 nm, in certain embodiments about 200 nm to about 350 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The dispersed aqueous phase of a HIPE may have water, and may also have one or more components, such as initiator, photoinitiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte may include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator may be present at up to about 20 mole percent based on the total moles of polymerizable monomers present in the oil phase. The initiator may be present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine)dihydrochloride, and other suitable azo initiators. To reduce the potential for premature polymerization which may clog the emulsification system, addition of the initiator to the monomer phase may be just after or near the end of emulsification.

Photoinitiators present in the aqueous phase may be at least partially water soluble and may have between about 0.05% and about 10%, and in certain embodiments between about 0.2% and about 10% by weight of the aqueous phase. Lower amounts of photoinitiator allow light to better penetrate the HIPE foam, which may provide for polymerization deeper into the HIPE foam. However, if polymerization is done in an oxygen-containing environment, there should be enough photoinitiator to initiate the polymerization and overcome oxygen inhibition. Photoinitiators may respond rapidly and efficiently to a light source with the production of radicals, cations, and other species that are capable of initiating a polymerization reaction. The photoinitiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane)dihydrochloride; 2,2'-Azobis[2-methyl-N-(2-hydroxyethyl)propionamide]; 2,2'-Azobis(2-methylpropionamidine)dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that may be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. The enrobeable elements may be treated to be made hydrophobic. The enrobeable elements may be treated to become hydrophilic.

The constituent fibers of the heterogeneous mass may be comprised of polymers such as polyethylene, polypropylene, polyester, and blends thereof. The fibers may be spunbound fibers. The fibers may be meltblown fibers. The fibers may comprise cellulose, rayon, cotton, or other natural materials or blends of polymer and natural materials. The fibers may also comprise a super absorbent material such as polyacrylate or any combination of suitable materials. The fibers may be monocomponent, bicomponent, and/or biconstituent, non-round (e.g., capillary channel fibers), and may have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers may range from about 0.1 denier to about 100 denier.

In one aspect, known absorbent web materials in an as-made may be considered as being homogeneous throughout. Being homogeneous, the fluid handling properties of the absorbent web material are not location dependent, but are substantially uniform at any area of the web. Homogeneity may be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability may be accomplished without a decrease in capillarity.

The heterogeneous mass may also include superabsorbent material that imbibe fluids and form hydrogels. These materials are typically capable of absorbing large quantities of body fluids and retaining them under moderate pressures. The heterogeneous mass may include such materials dispersed in a suitable carrier such as cellulose fibers in the form of fluff or stiffened fibers.

The heterogeneous mass may include thermoplastic particulates or fibers. The materials, and in particular thermoplastic fibers, may be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber may be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants may also be used. These surfactants may be applied to the thermoplastic fibers at levels of, for example, from about 0.2 to about 1 g. per sq. of centimeter of thermoplastic fiber.

Suitable thermoplastic fibers may be made from a single polymer (monocomponent fibers), or may be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention may include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON™, CELBOND™ or CHISSO™ bicomponent fibers). These bicomponent fibers may be concentric or eccentric. As used herein, the terms "concentric" and "eccentric" refer to whether the sheath has a thickness that is even, or uneven, through the cross-sectional area of the bicomponent fiber. Eccentric bicomponent fibers may be desirable in providing more compressive strength at lower fiber thicknesses. Suitable bicomponent fibers for use herein may be either uncrimped (i.e. unbent) or crimped (i.e. bent). Bicomponent fibers may be crimped by typical textile means such as, for example, a stuffer box method or the gear crimp method to achieve a predominantly two-dimensional or "flat" crimp.

The length of bicomponent fibers may vary depending upon the particular properties desired for the fibers and the web formation process. Typically, in an airlaid web, these thermoplastic fibers have a length from about 2 mm to about 12 mm long such as, for example, from about 2.5 mm to about 7.5 mm long, and from about 3.0 mm to about 6.0 mm long. Nonwoven fibers may be between 5 mm long and 75 mm long, such as, for example, 10 mm long, 15 mm long, 20 mm long, 25 mm long, 30 mm long, 35 mm long, 40 mm long, 45 mm long, 50 mm long, 55 mm long, 60 mm long, 65 mm long, or 70 mm long. The properties of these thermoplastic fibers may also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine may have a decitex in the range from about 1.0 to about 20 such as, for example, from about 1.4 to about 10, and from about 1.7 to about 7 decitex.

The compressive modulus of these thermoplastic materials, and especially that of the thermoplastic fibers, may also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers may be used to alter the properties, and especially the density characteristics, of the respective thermally bonded fibrous matrix.

The heterogeneous mass may also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON™ and KODEL™), high melting crimped polyester fibers (e.g., KODEL™ 431 made by Eastman Chemical Co.) hydrophilic nylon (HY-DROFIL™), and the like. Suitable fibers may also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length may vary depending upon the particular properties desired for these fibers. Typically they have a length from about 0.3 to 7.5 cm, such as, for example from about 0.9 to about 1.5 cm. Suitable nonbonding thermoplastic fibers may have a decitex in the range of about 1.5 to about 35 decitex, such as, for example, from about 14 to about 20 decitex.

The backsheet 207 may be positioned adjacent a garment-facing surface of the absorbent structure 205 and may be joined thereto by attachment methods (not shown) such as those well known in the art. For example, the backsheet 207 may be secured to the absorbent structure 205 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art. Forms of the present disclosure are also contemplated wherein the absorbent core 205 is not joined to the backsheet 207, the topsheet 203, or both.

The backsheet 207 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent core 205 from wetting articles of clothing which contact the feminine pad 10 such as undergarments. However, the backsheet 207 may permit vapors to escape from the absorbent structure 205 (i.e., is breathable). Thus, the backsheet 205 may comprise a polymeric film such as thermoplastic films of polyethylene or polypropylene. A suitable material for the backsheet 207 is a thermoplastic film having a thickness of from about 0.012 mm (0.5 mil) to about 0.051 mm (2.0 mils), for example. Any suitable backsheet known in the art may be utilized with the present invention.

The topsheet 203 is positioned adjacent a body-facing surface of the absorbent structure 205 and may be joined thereto and to the backsheet 207 by attachment methods (not shown) such as those well known in the art. Suitable attachment methods are described with respect to joining the backsheet 207 to the absorbent structure 205. The topsheet 203 and the backsheet 207 may be joined directly to each other in the feminine pad periphery and may be indirectly joined together by directly joining them to the absorbent structure 205 by the attachment methods.

The topsheet 203 may be compliant, soft feeling, and non-irritating to the wearer's skin. Further, the topsheet 203 may be liquid pervious permitting liquids (e.g., urine) to readily penetrate through its thickness. Some suitable examples of topsheet materials include films, nonwovens, laminate structures including film/nonwoven layers, film/film layers, and nonwoven/nonwoven layers. Other exemplary topsheet materials and designs are disclosed in provisional patent application Ser. No. 62/177,405 (filed Mar. 13, 2015), 62/168,199 (filed Mary 29, 2015), and 62/190,000 (filed Jul. 8, 2015).

The covers of the barrier cuffs of the present invention can be made of varying types of nonwovens of different MD and CD flexibility. The cover can be bonded to the topsheet of the absorbent article, such as, for example, by a slot coated stripe of adhesive, glue beads, ultrasonic sealing, or other suitable bonding agents. In certain forms of the present invention, the cover can be bonded to the backsheet at the side edges 22 and 24 (see FIG. 1) of the pad, such as, for example, using a crimp or other suitable bonding agents, such as, for example, adhesive.

In addition, in certain forms of the present invention, a portion 261 (See FIG. 2A) of the barrier cuff having the elastic members can then be folded back on itself and the folded back portion 261 can be glued continuously along the pad length. The folded back portion can then be bonded intermittently at the ends of the pad to the topsheet to prevent the barrier cuff from lifting at the ends of the pad while allowing it to lift in the central portion of the pad.

Elastic members may comprise any suitable elastic material. Some suitable examples include Spandex™ or other similar polyurethanes, natural or synthetic rubber, styrene block copolymers, metallocene polyolefins, Lycra™, or any other suitable elastomer materials known in the art. Preferably the elastic member is durable for ease of processing and for during the use of the article and exhibits excellent elasticity (recovery after strain) even under strains as high as 400%.

Additionally, the elastic members of the present disclosure may comprise any suitable dtex. Some exemplary dtex's are provided in the specific examples herein. In other forms, the elastic members may comprise a dtex of 680 or less. In some forms, the elastic members may have a dtex between 680 and 470, specifically including all numbers within the range and any ranges created thereby.

Referring back to FIG. 1, to construct the barrier cuffs 230A and 230B, the elastic members can be put under tension by stretching them. In certain forms of the present invention, each of the elastic members can be stretched to about 30% to about 400% engineering strain, such as, for example, from about 40% to about 300% engineering strain. In some forms, the engineering strain on the elastic members can be from about 45% to about 200%, from about 50% to about 150%, from about 55% to about 120%, from about 60% to about 90%, specifically including any numbers within these ranges and any ranges created thereby. In one example, the elastic can have a length of x and can be stretched an additional 1x such that the final stretched length of the elastic is 2x. In another example, the elastic can have a length of x and can be stretched an additional 2x such that the final stretched length of the elastic is 3x. In yet another example, the elastic can have a length of x and can be stretched an additional 1.5x such that the final stretched length is 2.5x. The elastic members are then attached to the cover, such as, for example, by gluing using elastic wrap adhesive or other suitable adhesives. In certain forms of the present invention, the glued length of the elastic members can be any suitable length, such as, for example, from about 100 to about 500 mm, from about 100 to about 400 mm, from about 100 to about 300 mm, from about 100 to about 200 mm, from about 150 to about 200 mm, or any other suitable length. When the elastic members are cut at the ends of the pad, they attempt to contract to their relaxed dimension. In typical diaper applications, the elastic members of their respective barrier cuffs are subjected to an engineering strain of over 200%.

In some forms of the present invention, the elastic members may comprise slow recovery elastic materials. For example, in some forms of the present invention the elastic members may exhibit a normalized unload force of greater than about 0.16 N/(g/m) at 37° C. as measured by the Two Cycle Hysteresis Test. Normalized unload forces of less than about 0.12 N/(g/m) at 37° C. are believed to be insufficient for use as an elastomer within absorbent articles. In some specific forms of the present invention, the elastic members exhibit a normalized unload force of greater than about 0.24 N/(g/m) at 37° C.

In contrast, the elastic members of the current invention exhibit a percent of initial strain of about 10% or greater after 15 seconds of recovery at 22° C., as measured by the Post Elongation Recovery Test. In other forms of the present invention, the elastic members exhibit a percent of initial strain of about 20% or greater after 15 seconds of recovery at 22° C. In other suitable forms of the present invention, the elastic members exhibit a percent of initial strain of about 30% or greater after 15 seconds of recovery at 22° C. In other suitable forms, the elastic members exhibit a percent of initial strain of about 40% or greater after 15 seconds of recovery at 22° C.

Furthermore, the elastic members of the present invention may exhibit a specified percent of initial strain at 22° C. after 30 seconds, 60 seconds, or three minutes of recovery. In certain forms, the elastic members may exhibit a percent of initial strain at 22° C. after 30 seconds of recovery of about 10% or greater. Alternatively, the elastic members may exhibit a percent of initial strain at 22° C. after 30 seconds of recovery about 15% or greater. In other forms of the present invention, the elastic members may exhibit a percent of initial strain at 22° C. after 60 seconds of recovery of about 10% or greater.

The elastic members may exhibit temperature responsiveness. In certain forms of the present invention, the elastic members exhibit a percent of initial strain at 32° C. after a specified amount of recovery time that is less than the percent of initial strain exhibited at 22° C. after the same recovery time. In one particular form of the present invention, temperature responsive elastic members may exhibit a reduction in a percent of initial strain after 15 seconds at 32° C. as compared to the percent of initial strain exhibited after 15 seconds at 22° C. (i.e., [percent of initial strain after 15 seconds of recovery at 22° C.]−[percent of initial strain after 15 seconds of recovery at 32° C.]). In some forms of the present invention, the difference is equal to or greater than 5%. In other forms of the present invention, the elastic members may exhibit a difference in the percent of initial strain after 15 seconds at 22° C. compared to after 15 seconds at 32° C. equal to or greater than 10%, 20%, 30%, or, alternatively, 40%. It is believed that elastic members exhibiting temperature responsiveness may further facilitate pad application. When the feminine pad is applied at about room temperature (i.e., approximately 22° C.), the elastic members may exhibit a relatively high percent of initial strain for a prescribed period of time, which allows the wearer to apply the pad. Upon application of the pad, the temperature of the elastic members will rise as a result of being in close proximity to the wearer's skin. As the temperature of the elastic members increases and nears skin temperature (i.e., approximately 32° C.), the percent of initial strain is reduced. Temperature responsiveness allows for application of the pad without "snap-back" while providing for increased recovery after application. Slow recovery elastics are discussed further in U.S. Pat. Nos. 7,717,893; 8,419,701; and 7,905,872.

In some forms of the present invention, the feminine pads may comprise wings. Wings can provide additional leakage protection for the feminine pad and can help secure the pad to the underwear of the user. Any suitable wing configuration known in the art may be utilized.

All the components can be adhered together with adhesives, including hot melt adhesives, as is known in the art. The adhesive can be Findlay H2128 UN or Savare PM 17 and can be applied using a Dynafiber HTW system.

Referring to FIGS. 1 and 2A, in use, the pad can be held in place by any support or attachment suitable for such purposes. In certain forms of the present invention, the pad is placed in the user's undergarment or panty and secured thereto by the fastening adhesive 211. The fastening adhesive 211 secures the pad in the crotch portion of the user's panty. A portion or all of the garment-facing surface 20B of the chassis 20 is coated with fastening adhesive 211. Any adhesive or glue suitable for such purposes can be used for the fastening adhesive 211 herein, such as, for example, using pressure-sensitive adhesive. Suitable adhesives include, for example, Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the absorbent article is placed in use, the pressure-sensitive adhesive is typically covered with a removable release liner in order to keep the adhesive from drying out or adhering to a surface other than the crotch portion of the panty prior to use. Suitable release liners are also described in U.S. Pat. Nos. 4,917,697 and 4,556,146. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad can be used by removing the release liner and thereafter placing the absorbent article in a panty so that the adhesive contacts the panty. The adhesive maintains the absorbent article in its position within the panty during use. The release liner can also be a wrapper that can individually package the pad.

EXAMPLES

Samples 1-2C were constructed in accordance with the present disclosure. Samples 3-7 are products which are currently available on the market.

Sample 1: A feminine pad approximately 270 mm long and comprising 2 fold lines. The first fold line being approximately 92 mm from the first end edge, and the second fold line being approximately 73 mm from the second end edge. The feminine pad further comprises:
(1) a nonwoven topsheet having a basis weight of 18 gsm of 50/50 polypropylene/polyethylene core/sheath configuration bicomponent fibers;
(2) a nonwoven secondary topsheet having a basis weight of 75 gsm and comprising 25 percent hollow spiral polyethylene terephthalate fibers of 10 dtex, 40 percent polypropylene fibers of 6.7 dtex, and 35 percent viscose rayon trilobal fibers of 3.3 dtex; the nonwoven secondary topsheet had a length of 218 mm and a width of 95 mm and was wrapped around item (4) such that opposite ends of the nonwoven secondary topsheet were positioned at the bottom of the item (4) and such that the nonwoven secondary topsheet was centered on item (4);
(3) an absorbent material—AGM at 1.8 grams distributed along the length and width of item (4);
(4) an Airlaid material having a basis weight of 345 gsm having pulp (treated and untreated), AGM (about 35% of the mass), as well as PET/PE core sheath bi-component fibers (which are thermally bonded) and latex binder. The whole material is embossed for further material stability; 59 mm wide and 218 mm long.
(5) a backsheet which is 14 gsm polypropylene film;
(6) barrier cuff—nonwoven first cover/second cover each having a basis weight of 14 gsm (glued continuously in MD to the topsheet at a spacing of 40 mm) and having an inner to inner spacing of about 34 mm (continuing to CD edges);
(7) barrier—cuff—elastic members of Lycra®—2 strands per cuff each having 470 dtex stretched about 60% each and glued for 120 mm (attachment approximately 85 mm from leading and 65 mm from trailing edge). Inner to inner elastic spacing of about 41 mm and spacing of about 4 mm between each strand in each cuff.

Sample 2A: A feminine pad approximately 400 mm long and comprising 2 fold lines. The first fold line being approximately 135 mm from the first end edge, and the second fold line being approximately 116 mm from the second end edge. The feminine pad further comprises:
(1) a nonwoven topsheet having a basis weight of 18 gsm of 50/50 polypropylene/polyethylene core/sheath configuration bicomponent fibers;
(2) a nonwoven secondary topsheet having a basis weight of 75 gsm and comprising 25 percent hollow spiral polyethylene terephthalate fibers of 10 dtex, 40 percent polypropylene fibers of 6.7 dtex, and 35 percent viscose rayon trilobal fibers of 3.3 dtex; the nonwoven secondary topsheet had a length of 339 mm and a width of 114 mm and was wrapped around item (4) such that opposite ends of the nonwoven secondary topsheet were positioned at the bottom of the item (4) and such that the nonwoven secondary top sheet was centered on item (4);
(3) an absorbent material—AGM at 5.7 grams distributed along the length and the width of item (4);
(4) an Airlaid material having a basis weight of 345 gsm having pulp (treated and untreated), AGM (about 35% of the mass), as well as PET/PE core sheath bi-component fibers (which are thermally bonded) and latex binder. The whole material is embossed for further material stability; 79 mm wide and 339 mm long.
(5) a backsheet which is 14 gsm polypropylene film;
(6) barrier cuff—nonwoven first cover/second cover each having a basis weight of 15 gsm (glue continuously in MD to the topsheet with a spacing of 72 mm and glued intermittently for about 63 mm at the ends of the product with a 60 mm spacing) and having an inner to inner spacing of about 54 mm (continuing to CD edges);
(7) barrier cuff—elastic members of Lycra®—2 strands per cuff each having 470 dtex stretched about 80% each and glued for 246 mm (attachment approximately 77 mm from each end). Inner to inner elastic spacing of about 61 mm and spacing of about 4 mm between each strand in each cuff.

Sample 2B: A feminine pad being approximately 348 mm long and comprising 2 fold lines. The first fold line being approximately 118 mm from the first end edge, and the second fold line being approximately 99 mm from the second end edge). The feminine pad further comprising:
(1) a nonwoven topsheet having a basis weight of 18 gsm of 50/50 polypropylene/polyethylene core/sheath configuration bi-component fibers;
(2) a nonwoven secondary topsheet having a basis weight of 75 gsm and comprising 25 percent hollow spiral polyethylene terephthalate fibers of 10 dtex, 40 percent polypropylene fibers of 6.7 dtex, and 35 percent viscose rayon trilobal fibers of 3.3 dtex; the nonwoven secondary topsheet had a length of 288 mm and a width of 104 mm and was wrapped around item (4) such that opposite ends of the nonwoven secondary topsheet were positioned at the bottom of the item (4) and such that the nonwoven secondary topsheet was centered on item (4);
(3) an absorbent material—AGM at 4.8 grams distributed along the length and width of item (4);
(4) an Airlaid material having a basis weight of 345 gsm having pulp (treated and untreated), AGM (about 35% of the mass), as well as PET/PE core sheath bi-component fibers (which are thermally bonded) and latex binder. The whole material is embossed for further material stability; 69 mm wide and 288 mm long.
(5) a backsheet which is 14 gsm polypropylene film;
(6) barrier cuff—nonwoven first cover/second cover each having a basis weight of 15 gsm (glue continuously in MD to the topsheet with a spacing of 62 mm and glued intermittently for about 63 mm at the ends of the product with a 50 mm spacing) and having an inner to inner spacing of about 44 mm (continuing to CD edges);
(7) barrier cuff—elastic members of Lycra®—2 strands per cuff each having 470 dtex stretched about 80% each and glued for 120 mm (attachment approximately 85 mm from the first end edge and 65 mm from second end edge). Inner to inner elastic spacing of about 51 mm and spacing of about 4 mm between each strand in each cuff.

Sample 2C: A feminine pad being approximately 348 mm long and comprising 2 fold lines. The first fold line being approximately 118 mm from the first end edge, and the second fold line being approximately 99 mm from the second end edge). The feminine pad further comprising:
(1) a nonwoven topsheet having a basis weight of 18 gsm of 50/50 polypropylene/polyethylene core/sheath configuration bi-component fibers;
(2) a nonwoven secondary topsheet having a basis weight of 75 gsm and comprising 25 percent hollow spiral polyethylene terephthalate fibers of 10 dtex, 40 percent polypropylene fibers of 6.7 dtex, and 35 percent viscose rayon trilobal fibers of 3.3 dtex; the nonwoven secondary topsheet had a length of 288 mm and a width of 69 mm; and was wrapped around item (4) such that opposite ends of the nonwoven secondary topsheet were positioned at the bottom of the item (4) and such that the nonwoven secondary top sheet was centered on item (4);

(3) an absorbent material—AGM at 7.2 grams distributed along the length and width of item (4);

(4) a nonwoven (SMS configuration) material of polypropylene having a basis weight of 10 gsm, a length of 288 mm and a width of 69 mm;

(5) an Airlaid material having a basis weight of 135 gsm having untreated pulp as well as PET/PE core sheath bi-component fibers (which are thermally bonded) and latex binder. The whole material is about 69 mm wide and 288 mm long.

(6) a backsheet which is 14 gsm polypropylene film;

(7) barrier cuff—nonwoven first cover/second cover each having a basis weight of 15 gsm (glue continuously in MD to the topsheet with a spacing of 62 mm and glued intermittently for about 63 mm at the ends of the product with a 50 mm spacing) and having an inner to inner spacing of about 44 mm (continuing to CD edges);

(8) barrier cuff—elastic members of Lycra®—2 strands per cuff each having 470 dtex stretched about 80% each and glued for 120 mm (attachment approximately 85 mm from the first end edge and 65 mm from second end edge). Inner to inner elastic spacing of about 51 mm and spacing of about 4 mm between each strand in each cuff.

Each of the above materials for each of the samples was adhesively joined to adjacent layers utilizing conventional adhesives with conventional adhesive application techniques at conventional adhesive basis weights respectively. With conventional basis weight and applications in absorbent articles, adhesives are believed to contribute to a very small extent of article stiffness as opposed to other components of the article. However, topsheet and the backsheet were thermally bonded to form the periphery of the article.

Sample 3: Always Discreet Moderate Absorbency, Regular Length.

Sample 4: Always Discreet Ultimate Absorbency, Long Length.

Sample 5: Poise Pads Moderate Absorbency, Regular Length.

Sample 6: Poise Overnight Pads, Ultimate Absorbency Long Length.

Sample 7: Poise Thin Shape Pads, Moderate Absorbency.

Data obtained from the above Samples regarding flexibility of the article is provided in Table 1. Samples 1 through 4 comprise barrier cuffs which have covers which are discrete and are attached to their respective top sheets. The anchor points for the covers and the elastic members for Samples 1 through 2C are inboard of the side edges of their respective absorbent cores. Samples 5 and 6 comprise barrier cuffs which comprise a portion of the topsheet and the backsheet. Anchor points for the elastic member are outboard of their respective absorbent cores. Sample 7 comprises barrier cuffs having discrete covers attached to the backsheet. Its elastic members are disposed outboard of the absorbent core.

TABLE 1

| Property | Sample No. | | | | | | | | |
| --- | --- | --- | --- | --- | --- | --- | --- | --- | --- |
| | 1 | 2A | 2B | 2C | 3 | 4 | 5 | 6 | 7 |
| Average Pad Thickness Central (mm) | 4.1 | 4.6 | 4.3 | 3.8 | 4.7 | 5.2 | 7.0 | 11.9 | 4.0 |
| Average Pad Length (mm) | 269.5 | 400.3 | 349.5 | 351.4 | 272.5 | 400.5 | 274.0 | 398.2 | 258.5 |
| EMS (mm) | 53.5 | 74.5 | 66.2 | 66.8 | 51.5 | 67.5 | 92.2 | 135.5 | 109.3 |
| Average Core Width @ Longitudinal Center (mm) | 63.0 | 82.5 | 73.8 | 69.6 | 65.3 | 84.5 | 74.2 | 79.2 | 65.2 |
| Average Core Width @ Front Fold (mm) | 62.0 | 82.7 | 74.7 | 70.0 | 68.3 | 89.7 | 73.0 | 103.2 | 73.5 |
| Average Core Width @ Back Fold (mm) | 62.2 | 82.8 | 74.8 | 69.8 | 65.7 | 87.7 | 73.2 | 89.8 | 79.5 |
| WER @ Longitudinal Center | 1.2 | 1.1 | 1.1 | 1.0 | 1.3 | 1.3 | 0.8 | 0.6 | 0.6 |
| WER @ Front Fold | 1.2 | 1.1 | 1.1 | 1.0 | 1.3 | 1.3 | 0.8 | 0.8 | 0.7 |
| WER @ Back Fold | 1.2 | 1.1 | 1.1 | 1.0 | 1.3 | 1.3 | 0.8 | 0.7 | 0.7 |
| LER | 5.0 | 5.4 | 5.3 | 5.3 | 5.3 | 5.9 | 3.0 | 2.9 | 2.4 |

Table 2 includes data with regard to the MD flexibility force and the CD flexibility force. Additionally, Table 2 include data with regard to the flexibility factor of the article. The flexibility factor takes into consideration the MD and CD flexibility. The flexibility factor is determined by the following equation.

$$\text{flexibility factor} = \sqrt{(\text{Average } CD \text{ Peak Load } MD \text{ flexibility})^2 + (\text{Average } MD \text{ Peak Load} CD \text{ flexibility})^2}$$

As noted previously, there are several factors which impact product curling during application. For example, the elastic forces exerted on the article by the barrier cuffs, as discussed previously is a factor. Elastic member engineering strain and elastic denier are also factors. Glue in length of the elastic member which extends from an outboard edge of an adhesive to an outboard edge of an adhesive in the first attachment zone and second attachment zone, respectively. Stiffness of the article as discussed previously, is also a factor. Core stiffness, e.g. all materials between the topsheet and backsheet, is believed to be the primary driver of article stiffness in both the MD and CD. While other materials like glues can play a role, these materials are believed to contribute to article stiffness to a much lesser extent than that of the absorbent core.

TABLE 2

| Property | Sample No. | | | | | | | | |
|---|---|---|---|---|---|---|---|---|---|
| | 1 | 2A | 2B | 2C | 3 | 4 | 5 | 6 | 7 |
| Average CD Peak Load (grams force) | 112.2 | 130.3 | 108.7 | 35.9 | 170.6 | 261.5 | 126.7 | 506.4 | 36.6 |
| Average MD Peak Load (grams force) | 162.8 | 166.3 | 134.7 | 45.2 | 177.7 | 281.4 | 150.7 | 595.0 | 45.1 |
| Flexibility factor (FF) | 197.7 | 211.3 | 173.1 | 57.7 | 246.4 | 384.2 | 196.9 | 781.3 | 58.1 |

Table 3 includes data with regard to the curl of the measured pads along with other measured features. The data in Table 3 includes spacing of the barrier cuffs, pad curl regarding front/back and left/right.

TABLE 3

| Property | Sample No. | | | | | | | | |
|---|---|---|---|---|---|---|---|---|---|
| | 1 | 2A | 2B | 2C | 3 | 4 | 5 | 6 | 7 |
| FL2 (mm) | 4.9 | 5.8 | 4.8 | 4.5 | 4.7 | 5.3 | 3.9 | 7.3 | 5.7 |
| FR2 (mm) | 4.5 | 5.0 | 4.9 | 4.5 | 4.5 | 5.3 | 4.7 | 7.7 | 5.8 |
| RL2(mm) | 3.8 | 5.4 | 4.1 | 4.0 | 4.3 | 5.4 | 3.7 | 6.6 | 4.7 |
| RR2 (mm) | 3.8 | 4.9 | 4.1 | 4.1 | 4.3 | 5.3 | 5.2 | 6.5 | 5.8 |
| (FL2 + FR2)/2 (mm) | 4.7 | 5.4 | 4.8 | 4.5 | 4.6 | 5.3 | 4.3 | 7.5 | 5.8 |
| (RL2 + RR2)/2 (mm) | 3.8 | 5.1 | 4.1 | 4.1 | 4.3 | 5.4 | 4.5 | 6.5 | 5.2 |
| FL (mm) | 6.0 | 6.9 | 5.7 | 5.5 | 6.0 | 6.0 | 7.5 | 11.6 | 15.5 |
| FR (mm) | 5.0 | 6.6 | 5.2 | 5.0 | 5.8 | 5.7 | 7.3 | 11.8 | 8.8 |
| RL (mm) | 5.8 | 6.1 | 5.7 | 5.5 | 5.8 | 6.7 | 7.2 | 12.3 | 16.5 |
| RR (mm) | 5.5 | 6.2 | 5.6 | 5.8 | 6.0 | 6.8 | 8.0 | 13.7 | 11.3 |
| (FL + FR)/2(mm) | 5.5 | 6.8 | 5.5 | 5.2 | 5.9 | 5.8 | 7.4 | 11.7 | 12.2 |
| (RL + RR)/2(mm) | 5.7 | 6.1 | 5.6 | 5.6 | 5.9 | 6.7 | 7.6 | 13.0 | 13.9 |
| FPC (mm) | 0.8 | 1.4 | 0.6 | 0.7 | 1.3 | 0.5 | 3.1 | 4.2 | 6.4 |
| RPC (mm) | 1.9 | 1.0 | 1.5 | 1.6 | 1.6 | 1.4 | 3.1 | 6.4 | 8.6 |
| APC (mm) | 1.3 | 1.2 | 1.1 | 1.1 | 1.4 | 1.0 | 3.1 | 5.3 | 7.5 |

Figure 9:
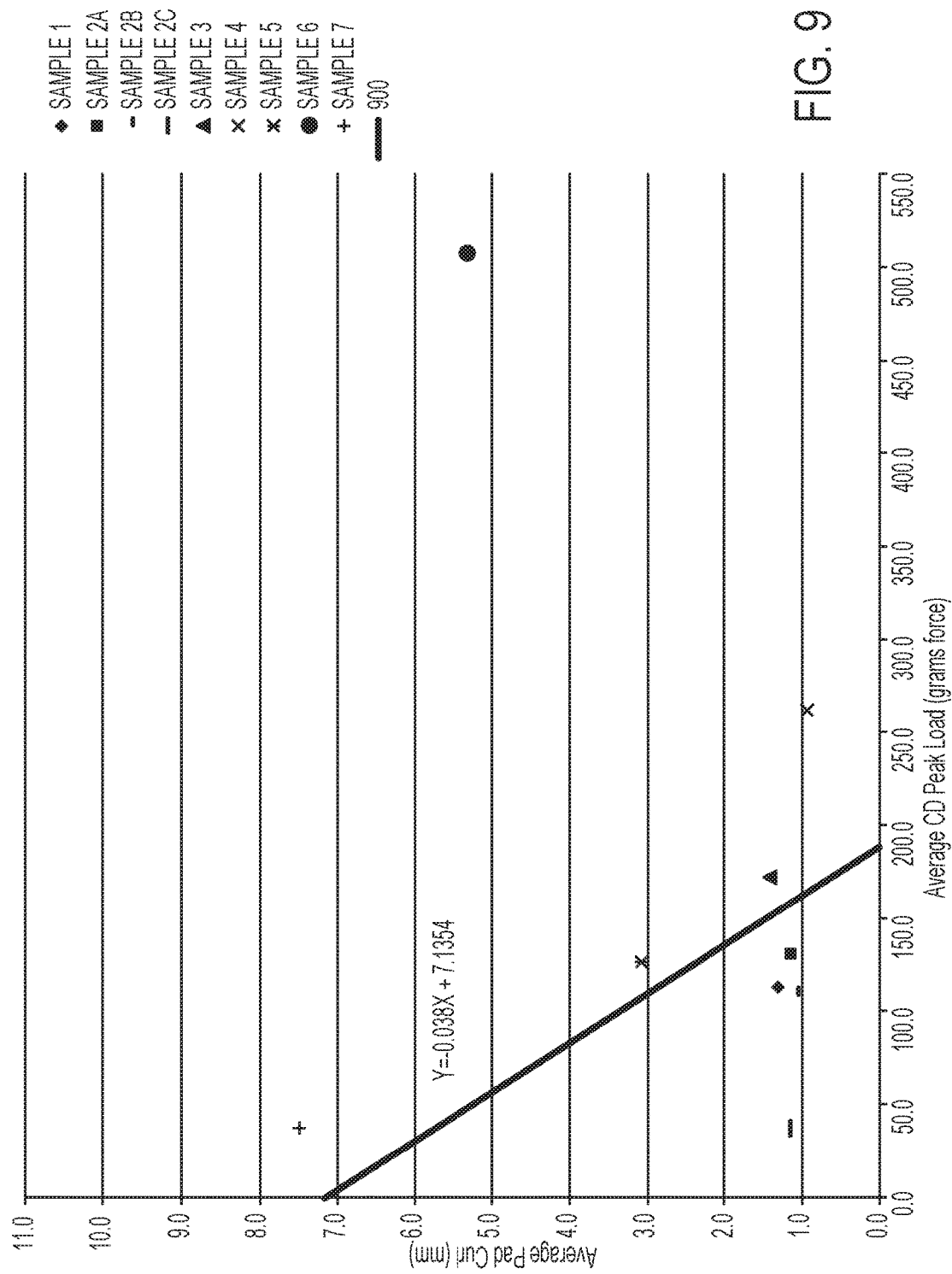
FIG. 9 is a graph depicting average pad curl versus the average cross direction peak load of a plurality of measured samples.

In some forms, the average of the front pad curl (FPC) and rear pad curl (RPC)—average pad curl (APC)—in mm versus the average CD peak load in grams force is shown in the graph shown in FIG. 9. In some forms, the APC may satisfy the following equation with regard to CD peak load.

$$APC \leq (-0.038 \text{Average CD Peak Load} + 7.1354)$$

Line 900 is provided for ease of visualization.

In such forms, the APC may be less than about 7.0 mm, less than about 6.0 m, less than about 5.0 mm, less than about 4.0 mm, or less than about 3.0 mm, specifically including all numbers within these ranges and any ranges created thereby. In one specific example, the APC may be from between about 0.5 mm to about 3.0 mm or from about 1.0 mm to about 2.5 mm, specifically including all numbers within these ranges and any ranges created thereby. In such forms, the cross directional peak load may be less than about 188 grams force, less than about 170 grams force, less than about 160 grams force, less than about 130 grams force, or less than about 120 grams force, specifically including all numbers within the range and any ranges created thereby. In one specific example, the cross directional peak load may be from between about 30 grams force to about 188 grams force or from about 35 grams force to about 170 grams force, specifically including all numbers within these ranges and any ranges created thereby.

Figure 10:
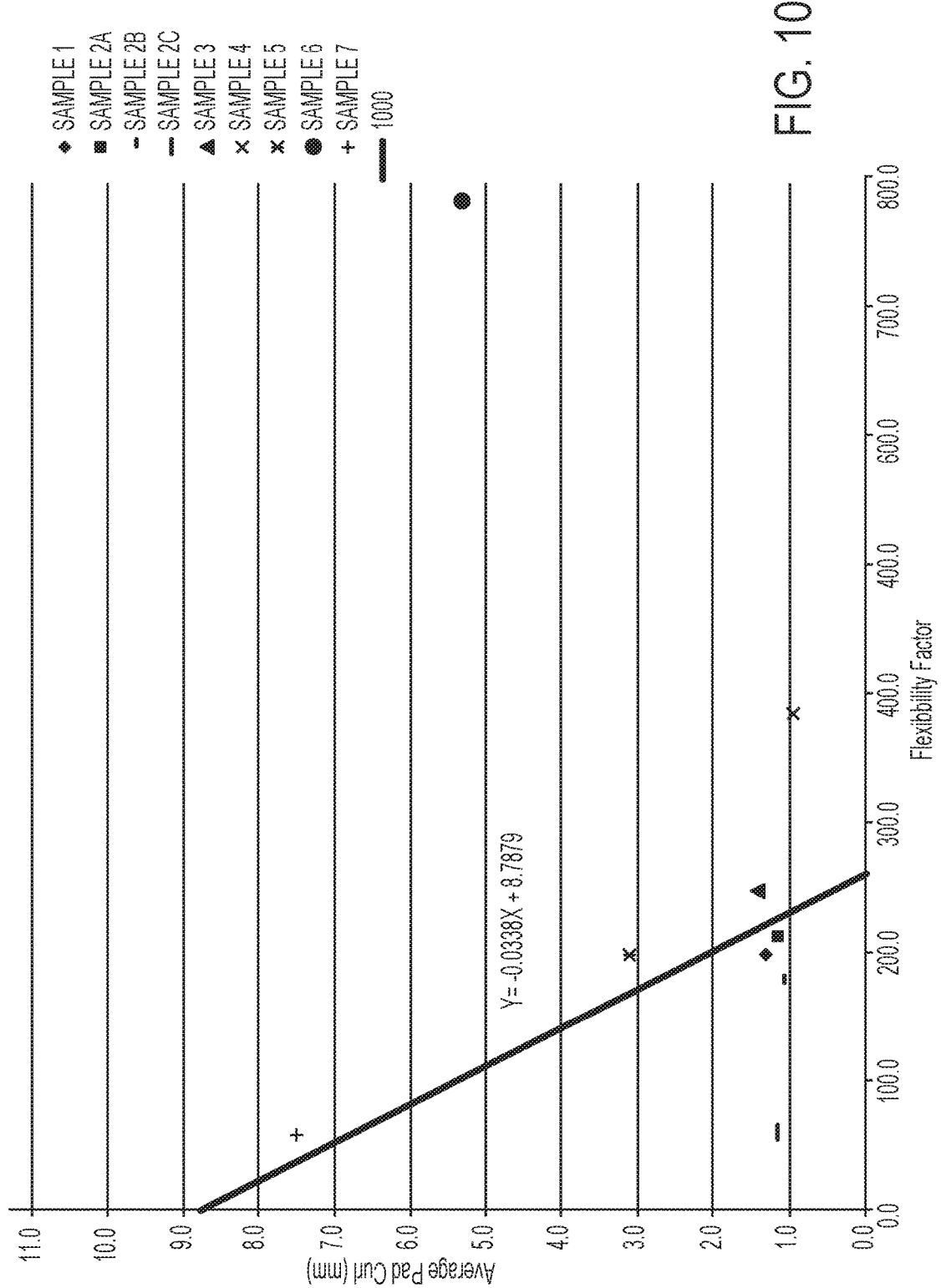
FIG. 10 is a graph depicting average pad curl versus the flexibility factor of a plurality of measured samples.

In some forms, the APC in mm versus the Flexibility Factor is shown in the graph of FIG. 10. In some forms, the APC may satisfy the following equation with regard to flexibility factor.

$$APC \leq (-0.0338 FF + 8.7879)$$

Line 1000 is provided for ease of visualization.

In such forms, the APC may be less than about 9.0 mm, less than about 8.0 mm, less than about 7.0 mm, less than about 6.0 mm, less than about 5.0 mm, less than about 4.0 mm or less than about 3.0 mm, specifically including all numbers within these ranges and any ranges created thereby. In one specific example, the APC may be from between about 0.5 mm to about 3.0 mm or from about 1.0 mm to about 2.5 mm, specifically including all numbers within these ranges and any ranges created thereby. In such forms, the flexibility factor may be less than about 260, 250, 240, 230, 220, 210, 200, or 190, specifically including all numbers within these ranges and any ranges created thereby. In one specific example, the flexibility factor may be from between about 30 to about 260, 40 to 240, or 50 to 220, specifically including all numbers within these ranges and any ranges created thereby.

Based on the data above, in some forms, the APC may be less than about 3.0 mm or less than about 2.0 mm, specifically including all numbers within these ranges and any ranges created thereby. In some specific examples, the APC may be between about 0.5 mm to about 2.5 mm or from between about 1.0 mm to about 2.0 mm, specifically including all numbers within these ranges and any ranges created thereby. In such forms, the flexibility factor may be less than about 240, 230, 220, or 212 specifically including any numbers within these ranges and any ranges created thereby. In one specific example, a disposable absorbent article may comprise a flexibility factor of between about 50 to about 220, specifically including all numbers within the range and any ranges created thereby. In addition to the flexibility factor or independently therefrom, in such forms, the average cross directional peak load may be less than about 160 grams force, less than about 150 grams force, or less than about 120 grams force, specifically including all numbers within these ranges and any ranges created thereby. In one specific example, the average cross directional peak force may be from between about 20 grams force to about 160 grams force, about 30 grams force to about 150 grams force, or between about 35 grams force to about 135 grams force, specifically including all numbers within the range and any ranges created thereby. Similarly, in addition to the flexibility factor and/or the cross directional peak load or independently thereof, in such forms, the average machine direction peak load may be less than about 170 grams force, less than about 160, less than about 150, or less than about 140, specifically including all numbers within these ranges and any ranges created thereby. In one example, the average machine direction peak load may be from between about 40 to about 170 grams force, specifically including all numbers within the range and any ranges created thereby.

In yet other forms, the APC may be less than about 7.5 mm, less than about 7.0 mm, less than about 4.0 mm, or less than about 3.0 mm, specifically including all numbers within these ranges and any ranges created thereby. In one specific example, the APC may be from between about 0.5 mm to about 4.0 mm or from about 1.0 mm to about 3.0 mm, specifically including all numbers within these ranges and any ranges created thereby. In such forms, the flexibility factor may be less than 190, 180, 170, 160, or 150, specifically including all numbers within these ranges and any ranges created thereby. In one specific example, the flexibility factor may be from between about 50 to about 190, specifically including all numbers within this range and any ranges created thereby. In addition to the flexibility factor or independently therefrom, in such forms, the average cross directional peak load may be less than about 120 grams force less than about 115 grams force, or less than about 110 grams force, specifically including all numbers within these ranges or any ranges created thereby. In one specific example, the average cross directional peak load may be from between about 30 grams force to about 120 grams force or from about 35 grams force to about 115 grams force, specifically including all numbers within these ranges and any ranges created thereby.

Still in other forms, the APC may be less than about 3.0 mm or less than about 2.0 mm, specifically including all numbers within these ranges and any ranges created thereby. In some specific examples, the APC may be between about 0.5 mm to about 2.5 mm or from between about 1.0 mm to about 2.0 mm, specifically including all numbers within these ranges and any ranges created thereby. In such forms, the cross directional peak load may be less than about 160 grams force, less than about 150 grams force, less than about 140 grams force, less than 130 grams force, or less than about 120 grams force, specifically including all numbers within these ranges and any ranges created thereby. In one specific example, the average cross directional peak force may be from between about 20 grams force to about 160 grams force, about 30 grams force to about 150 grams force, or between about 35 grams force to about 135 grams force, specifically including all numbers within the range and any ranges created thereby. In such forms, the flexibility factor may be less than about 380, less than about 370, less than about 350, less than about 300, less than about 280, less than about 250, or less than about 220, specifically including all numbers within these ranges and any ranges created thereby. In one specific example, a disposable absorbent article may comprise a flexibility factor of between about 30 to about 380, 50 to about 340, 55 to about 330, or from about 40 to 220, specifically including all numbers within the range and any ranges created thereby.

Test Methods:

Basis Weight Method

Basis weights of materials described herein may be determined by several available techniques, but a simple representative technique involves taking an absorbent article or other consumer product, removing any elastic which may be present and stretching the absorbent article or other consumer product to its full length. A punch die having an area of 45.6 cm$^2$ is then used to cut a piece of the material to be analyzed (e.g., topsheet or backsheet) from the approximate center of the absorbent article or other consumer product in a location which avoids to the greatest extent possible any adhesive which may be used to fasten the material to any other layers which may be present and removing the material from other layers (using cryogenic spray, such as Cyto-Freeze, Control Company, Houston, Tex., if needed). The sample is then weighed and dividing by the area of the punch die yields the basis weight of the material. Results are reported as a mean of 5 samples to the nearest 0.1 cm$^2$.

Pad Curl and Other Measurements

Samples are conditioned at 23° C.±2° C. and 50%±2% relative humidity for 2 hours prior to testing. The test is run under the same environmental conditions. All linear measurements are made using a calibrated steel metal ruler traceable to NIST or other standards organization. Caliper measurements are made using a Schiefer Standard Spring Compressometer (available from Frazier Precision Instrument Co., Hagerstown Md.) or equivalent. The compressometer was used with a 4.75 mm diameter ball as the foot. Herein front, rear, left and right refer to the products orientation on the wearer's body.

The article is removed from its wrap and if present, the release paper of the removed article to expose the panty fastening adhesive (PFA). Apply talc powder to the PFA on the back sheet to mitigate tackiness. Suspend the article vertically by its front leading edge. Attach a 500 g±1 g weight to the rear leading edge allowing the article to hang freely. After 30 sec measure the length of the article along the longitudinal centerline of the article to the nearest 0.1 mm and record as the Article Length (AL).

The article is mounted on a flat metal plate approximately 3 mm in thickness, and length and width dimensions are larger than the article. Using 2.54 cm wide masking tape, secure the article to the center of the metal plate. The tape is attached along the longitudinal centerline at front edge with 1 cm of the tape overlapping the articles edge. In like fashion the rear edge is secured to the plate such that the article is extended to the previously measured AL for that article. After mounting the article caliper measurements are done without undue delay.

Caliper measures for the Front Pad Curl (FPC) are made on the front 30% of the article. The front of the article corresponds to that portion of the article that would be associated with the anterior portion of the body during normal use. Place the metal plate under the foot. Slowly lower the foot until the foot visually touches the plate. Zero the lower caliper gauge of the compressometer. Next place the front left corner of the article under the foot. Visually select a site within 1 cm of the left distal side of the absorbent body that is the greatest elevation from the metal plate. Slowly lower the foot until the foot visually touches the top sheet of the article and record the caliper (FL) to the nearest 0.1 mm. Move the mounted article so that the front right corner is under the foot. Visually select a site within 1 cm of the right distal side of the absorbent body that is the greatest elevation from the metal plate. Slowly lower the foot until the foot visually touches the top sheet and record the caliper (FR) to the nearest 0.1 mm. Take a piece of masking tape longer than the width of the article, and place it across the article perpendicular to longitudinal centerline of the article and aligned immediately inboard of the absorbent body to tack down any pad curl. Again place the front left corner of the article under the foot. Select a site that is 5 mm inboard of the masking tape and 5 mm inboard of the edge of the absorbent body. Slowly lower the foot until the foot visually touches the top sheet and record the caliper (FL2) to the nearest 0.1 mm. Move the mounted article so that the front right corner is under the foot. Select a site 5 mm inboard of the masking tape and 5 mm inboard of the edge of the absorbent body. Slowly lower the foot until the foot visually touches the top sheet and record the caliper (FR2) to the nearest 0.1 mm. Calculate the Front Pad Curl (FPC) as $[((FL+FR)/2)-(FL2+FR2)/2]$ and report to the nearest 0.1 mm. The Rear Pad Curl (RPC) is measured and calculated in like fashion (on the rear 30% of the article) and also record to the nearest 0.1 mm. Calculate the Rear Pad Curl (RPC) as $[((RL+RR)/2)-(RL2+RR2)/2]$ and report to the nearest 0.1 mm. Calculate Average Pad Curl as (FPC+RPC)/2 and report to the nearest 0.1 mm.

Remove the article from the metal plate and remount the article at the correct AL extension to a light box that is larger than the size of the article. Mark the intersection of the longitudinal and lateral centerline of the article. Using a calibrated ruler measure the distance along the lateral centerline between the outermost elastic member left of the longitudinal centerline to the outermost elastic member right of the longitudinal centerline to the nearest 0.1 mm. Record as the Elastic Member Spacing (EMS). Also measure the width of the absorbent body along the lateral centerline and record to the nearest 0.1 mm. Record as the Core Width (CW). Calculate a Length to Elastic Ratio (LER) by dividing the AL by the EMS and record to the nearest 0.1 mm. Calculate a Width to Elastic Ratio (WER) by dividing the CW by the EMS and record to the nearest 0.1 mm.

Repeat measurements on a total of six replicate pads. Calculate the arithmetic mean for all Front Pad Curl (FPC), Rear Pad Curl (RPC), Length to Elastic Ratio (LER), and Width to Elastic Ratio (WER). Report all values to the nearest 0.1 mm.

MD/CD Flexibility
Equipment Preparation:

The bending properties of a sample are measured on a constant rate of extension tensile tester (a suitable instrument is the MTS Alliance using Testworks 4.0 Software, as available from MTS Systems Corp., Eden Prairie, Minn.) using a load cell for which the forces measured are within 10% to 90% of the limit of the cell. All testing is performed in a room controlled at 23° C.±3° C. and 50%±2% relative humidity.

Figure 8:
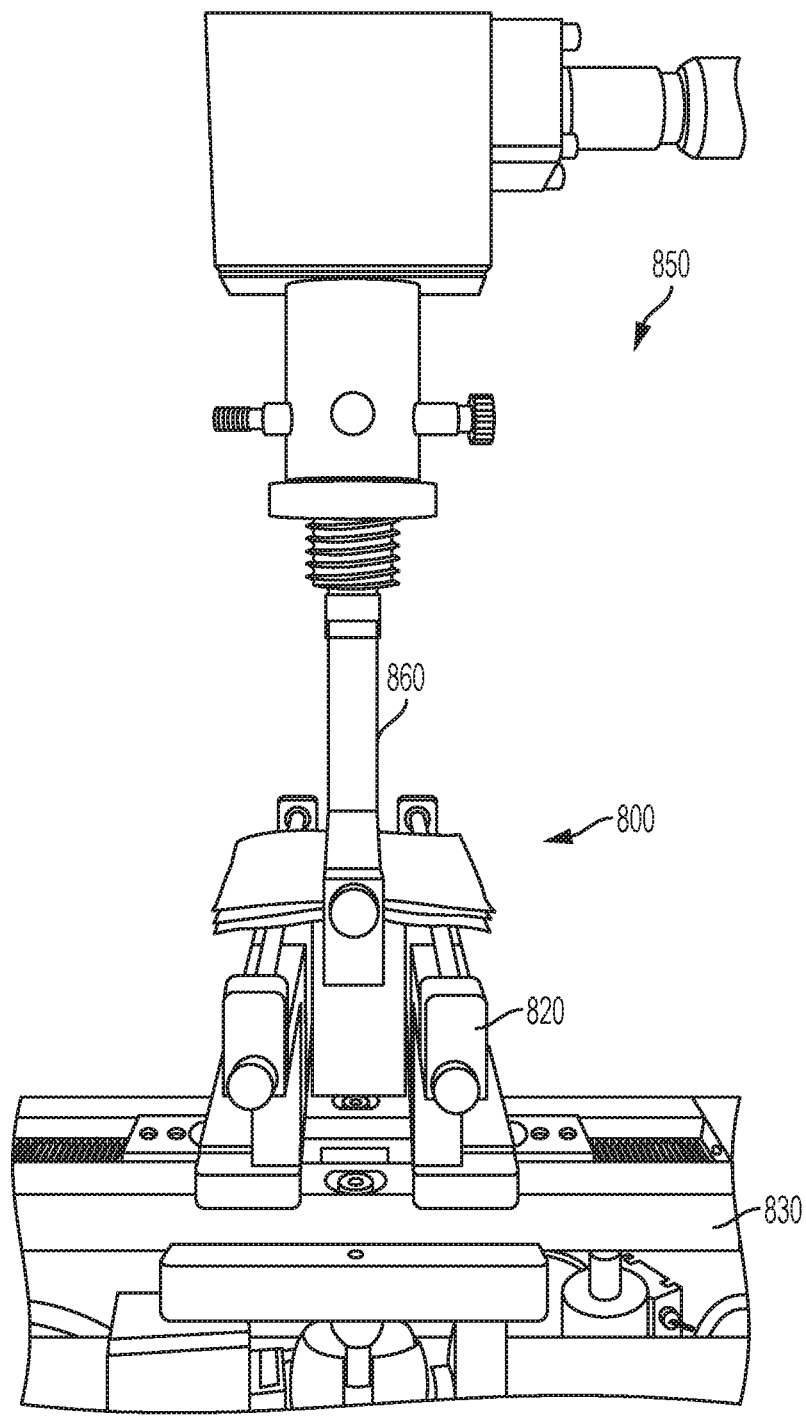
FIG. 8 depicts a portion of a testing apparatus which is utilized to measure properties of a sample regarding a machine direction and a cross machine direction.

Referring to FIG. 8, a bottom stationary fixture 800 comprising two bars 3.175 mm in diameter by 60 mm in length, made of polished stainless steel are each mounted on their own fork 820. These 2 bars are mounted horizontally, aligned front to back and parallel to each other, with top radii of the bars vertically aligned. Furthermore, the fixture 800 allows for the two bars to be moved horizontally away from each other on a track 830 so that a gap can be set between the bars while maintaining their orientation. A top movable fixture 850 comprises a third bar also 3.175 mm in diameter by 60 mm in length, made of polished stainless steel mounted on a fork 860. The bar of the top fixture 860 should be parallel to, and aligned front to back with the bars of the bottom fixture 800. Both fixtures 800 and 860 include an integral adapter appropriate to fit the respective position on the tensile tester frame and lock into position such that the bars are orthogonal to the motion of the crossbeam of the tensile tester.

Set the gap between the bars of the lower fixture 800 to 30 mm±0.5 mm (center of bar to center of bar) with the upper bar centered at the midpoint between the lower bars. Set the gage (bottom of top bar to top of lower bars) to 1.0 cm.

Sample Preparation:

Samples are conditioned at 23° C.±3° C. and 50%±2% relative humidity two hours prior to testing. The article is removed from its wrap and if present, the release paper of the removed article to expose the panty fastening adhesive (PFA). Apply talc powder to the PFA on the back sheet to mitigate tackiness. Cut a square specimen 50 mm in the longitudinal direction of the article (MD) and 50 mm in the lateral direction (CD) of the article from the center of the article. Sample should offset from any folds that are present in the article. The orientation of the sample should be maintained such that the MD direction and the CD direction, each of which is imputed from the article to the sample, is preserved maintaining their orientation after they are cut. Measure the caliper of each specimen, using a digital caliper (e.g. Ono Sokki GS-503 or equivalent) fitted with a 25 mm diameter foot that applies a confining pressure of 0.1 PSI. Read the caliper (mm) 5 sec after resting the foot on the sample and record to the nearest 0.01 mm.

Program the tensile tester for a compression test, to move the crosshead down at a rate of 0.5 mm/sec until the upper bar touches the top surface of the specimen, then continue for an additional 14 mm collecting force (N) and displacement (m) data at 25 Hz, and return the crosshead to its original gage. Load a specimen such that it spans the two lower bars and is centered under the upper bar with its sides parallel to the bars. Zero the crosshead and load cell. Start the run and collect data. The orientation of the sample on the bottom fixture 800 should be recorded and associated with obtained data in the particular orientation. Where the sample is oriented such that the MD direction is perpendicular to the long axis of the bars of the bottom fixture 800, the data being obtained is with regard to the MD direction of the article. Similarly, where the sample is oriented such that the CD direction is perpendicular to the long axis of the bars of the bottom fixture 800, the data being obtained is with regard to the CD direction of the article.

Construct a graph of force (N) verses displacement (mm). Read the Maximum Peak Force (N) from the graph and record to the nearest 0.1N. Calculate the Flexural Strength of the specimen as the Maximum Peak Force (N)/Sample Area (m$^2$) and report to the nearest 0.1 kPa. Calculate the Handleability as [0.5× Maximum Peak Force (N)× Displacement at Peak (mm)]/Specimen Caliper (mm) and record to the nearest 0.01N.

Measures are repeated in like fashion for 10 MD and 10 CD samples and report the average separately for each of the ten values to the nearest 0.1 N for Peak Force, 0.1 kPa for Flexural Strength, and 0.01N for Handleability.

Post Elongation Recovery

This method is used to determine the post elongation strain of barrier cuffs as a function of temperature and time. The measurement is done at 22° C. (72° F.) or at 32° C. (90° F.). The measurement at 22° C. (72° F.) is designed to simulate the recovery of the barrier cuffs at room temperature, while the measurement at 32° C. (90° F.) is designed to measure the recovery of the elastic members near skin temperature. A two-step analysis, Stretch and Recovery, is performed on the samples. The method employs a Dynamic Mechanical Analyzer. A TA Instruments DMA 2980 (hereinafter "DMA 2980"), available from TA Instruments, Inc., of New Castle, Del.; equipped with a film clamp, Thermal Advantage/Thermal Solutions software for data acquisition, and Universal Analysis 2000 software for data analysis was used herein. Many other types of DMA devices exist, and the use of dynamic mechanical analysis is well known to those skilled in the art of polymer and copolymer characterization.

Methods of operation, calibration and guidelines for using the DMA 2980 are found in TA Instruments DMA 2980 Operator's Manual issued March 2002, Thermal Advantage User's Reference Guide issued July 2000 and Universal Analysis 2000 guide issued February 2003. To those skilled in the use of the DMA 2980, the following operational run conditions should be sufficient to replicate the stretch and recovery of the samples.

The DMA 2980 was configured to operate in the Controlled Force Mode with the film clamp. The film clamp is mounted onto the DMA 2980 and calibrated according to the User's Reference Guide. The barrier cuff to be tested is cut into samples of substantially uniform dimension. For the DMA 2980, suitable sample dimensions are approximately 20 mm×6.4 mm×1.0 mm (length×width×thickness). The sample thickness is dependent on the materials and structure of the barrier cuff and on the confining pressure used to measure the thickness. TA Instruments recommends the sample thickness, when securely mounted within the film clamps, to be less than or equal to about 2.0 mm. The lower film clamp of the DMA 2980 is adjusted and locked in a position which provides approximately 10 mm between the clamping surfaces. The sample is mounted in the film clamps and the lower clamp is allowed to float to determine the gauge length between the film clamps. The sample ID and dimensions are recorded. The film clamp is locked in position and the furnace is closed.

Stretch Method—

For the sample dimensions specified above, the DMA 2980 is configured as follows: Preload force applied to sample in clamp (0.01N); auto zero displacement (on) at the start of the test; furnace (close), clamp position (lock), and temperature held at $T_i$ (22° C. or 32° C.) at the end of the stretch method. Data acquisition rate is set at 0.5 Hz (1 point per 2 seconds). The stretch method is loaded onto the DMA 2980. The method segments are (1) Initial Temperature $T_i$ (22° C. or 32° C.), (2) Equilibrate at $T_i$, (3) Data Storage ON, and (4) Ramp Force 5.0 N/min to 18.0 N.

Upon initiation of the test, the temperature ramps to the specified $T_i$ (22° C. or 32° C.) [method segment 1], and the temperature is maintained at this $T_i$ [method segment 2]. After a minimum of 15 minutes at $T_i$, the operator initiates the sample stretching and concurrent data collection [method segments 3 and 4]. The sample is stretched with an applied ramp force of 0.8 N/min per millimeter of initial sample width (e.g., for the sample dimensions specified above, the applied ramp force is 5 N/minute) to approximately 30 mm in length. The gradual increase in force more closely simulates application of the article and prevents sample breakage. The sample is locked in place at the stretched length of approximately 30 mm and maintained at $T_i$. The force required to stretch the barrier cuff to a length of approximately 30 mm and the percent strain of the laminate at this length are recorded manually from the digital readout on the instrument. The percent strain is calculated by subtracting the gauge length from the stretched length, then dividing the result by the gauge length and multiplying by 100. The initial percent strain is described by the equation below:

$$\text{Initial Percent Strain} = \% \text{ Strain}_i = 100 * ((Ls - L_g)/L_g)$$

where $L_g$ is the length of the gathered stretch laminate in a relaxed state and Ls is the length of the stretched laminate between the film clamps at the end of the stretch step of the analysis (~30 mm). % $\text{Strain}_i$ is the percent strain of the stretch laminate at the start of the recovery method (i.e. after the stretch part of the method is complete). A sample stretched from a gauge length of 10 mm to a length of 30 mm results in a percent strain of 200%.

For purposes of this test, the maximum percent strain (e.g., 200%, 150%, or 100%) is to be chosen such that the strain does not result in irreversible deformation, delamination, or tearing of the barrier cuff. If the barrier cuff has an extensibility of less than 200% engineering strain (±5%), a new specimen of the sample is stretched from a gauge length of 12 mm to an extended length of 30 mm which results in a percent strain of 150% engineering strain. If the barrier cuff has an extensibility of less than 150% engineering strain (±5%), a new specimen of the sample is stretched from a gauge length of 15 mm to an extended length of 30 mm which results in a percent strain of 100% engineering strain. Testing of barrier cuffs with maximum extensibility of <100% is also within the scope of this method. For barrier cuffs tested at an initial percent strain of 100% or less, the post elongation strain is reported as the percent strain rather than the percent of initial % strain at the different times of recovery (15 seconds, 30 seconds, 60 seconds and 3 minutes).

For samples of different dimensions, the applied force to stretch the sample is adjusted to achieve an applied ramp force of 0.8 N/min per millimeter of initial sample width. For example, a force ramp of 2.5 N/min is applied to a sample with an initial width of 3.2 mm. For samples of different lengths, the total displacement during the elongation is adjusted to achieve an initial percent strain of 200% (or less if the sample has limited extensibility, i.e. 150% or 100% strain).

Recovery Method—

The Recovery Method is loaded onto the instrument and initiated approximately 15 seconds after reaching the desired initial percent strain (i.e. 200%, 150%, or 100%) in the Stretch Method. The four segments of the recovery method are (1) Data Storage ON, (2) Force 0.01N, (3) Ramp to $T_i$, and (4) Isotherm for 3.0 minutes. The following DMA 2980 parameter setting is changed from the Stretch Method: auto zero displacement is changed to (OFF). The Recovery Method measures the length of the sample over a 3 minute time period at the specified temperature ($T_i$=either 22° C. or 32° C.). The sample length, percent strain, and test temperature are recorded as a function of recovery time. The post elongation strain is reported as the percent of the initial percent strain after different times of recovery (15 seconds, 30 seconds, 60 seconds, and 3 minutes).

For samples of different dimensions, the force applied to the sample during recovery (segment 2 above) is adjusted to achieve an applied force of 0.0016 N per millimeter of initial sample width (0.01N for 6.4 mm wide sample). For example, a force of 0.005 N is applied to a sample 3.2 mm wide.

Two Cycle Hysteresis Test

This method is used to determine properties that may correlate with the forces experienced by the consumer during application of the product containing the slow recovery barrier cuffs and how the product fits and performs once it is applied.

The two cycle hysteresis test method is performed at room temperature (21° C./70° F.) and also at body temperature (37° C./99° F.). The barrier cuff to be tested is cut into a sample of substantially rectilinear dimensions. Sample dimensions are selected to achieve the required strain with forces appropriate for the instrument. Suitable instruments for this test include tensile testers commercially available from MTS Systems Corp., Eden Prairie, Minn. (e.g. Alliance RT/1 or Sintech 1/S) or from Instron Engineering Corp., Canton, Mass. The sample thickness is dependent on the materials and structure of the barrier cuff and on the confining pressure used to measure the thickness. The thicknesses of samples are typically 0.5 mm to 5 mm thick measured with 0.2 psi confining pressure. However, testing of barrier cuffs with different thicknesses (e.g., <0.5 mm or >5 mm) is within the scope of this method.

The following procedure illustrates the measurement when using the above sample dimensions and either an Alliance RT/1 or Sintech 1/S. The instrument is interfaced with a computer. TestWorks 4™ software controls the testing parameters, performs data acquisition and calculation, and provides graphs and data reports.

The widths of the grips used for the test are greater than or equal to the width of the sample. Typically 1" (2.54 cm) wide grips are used. The grips are air actuated grips designed to concentrate the entire gripping force along a single line perpendicular to the direction of testing stress having one flat surface and an opposing face from which protrudes a half round (radius=6 mm) to minimize slippage of the sample. In the case of the measurement at 37° C., the upper grip is a lightweight grip with serrated faces.

The load cell is selected so that the forces measured will be between 10% and 90% of the capacity of the load cell or the load range used. Typically a 25 N load cell is used. The fixtures and grips are installed. The instrument is calibrated according to the manufacturer's instructions. The distance between the lines of gripping force (gauge length) is 2.50" (63.5 mm), which is measured with a steel ruler held beside the grips. The load reading on the instrument is zeroed to account for the mass of the fixture and grips. The specimen is equilibrated a minimum of 1 hour at 21° C. before testing. The specimen is mounted into the grips in a manner such that there is no slack and the load measured is between 0.00 N and 0.02 N. The instrument is located in a temperature-controlled room for measurements performed at 21° C. A suitable environmental chamber is used to maintain the testing temperature for measurements performed at 37° C.; the sample is mounted in the grips and equilibrated for 5 minutes at 37° C. before starting the test.

The 2 cycle hysteresis test method involves the following steps:

(1) Strain the sample to the specified initial percent strain (i.e., Strain=150%) at a constant crosshead speed of 20"/min. (50.8 cm/min) with no hold.
(2) Reduce the strain to 0% strain (i.e., return grips to the original gauge length of 2.50") at a constant crosshead speed of 3"/min. (7.62 cm/min) with no hold.
(3) Strain the sample to $Strain_i$, at a constant crosshead speed of 20"/min. (50.8 cm/min) with no hold.
(4) Reduce strain to 60% strain at a constant crosshead speed of 3"/min. (7.62 cm/min)
(5) Hold the sample at 60% strain for 5 minutes.
(6) Go to 0% strain at a constant crosshead speed 3"/min. (7.62 cm/min)

The reported unload force is the measured unload force of the barrier cuff (BC) at 60% strain after the 5 minute hold in step 5, normalized to Newton per 1 meter width of BC* basis weight of elastomer+adhesive (E+A) in the BC, N/(m·gsm)= N/(g/m), as shown in the equation below. The basis weight of the elastic and adhesive in the BC is calculated by dividing the grams of elastomer+adhesive in the BC by the area of the BC fully extended. The area of the fully extended barrier cuff ($A_{FEBC}$) is defined as the area of the substrate of the barrier cuff in the absence of elastic and adhesive. The normalized unload force in $$N/(m \cdot gsm) = N/(g/m) = \frac{\text{measured unload force (N)}}{[\text{width of } BC \text{ in meters} * ((\text{grams of } E+A) \div A_{FEBC} \text{ in m}^2)]}.$$

For different sample dimensions, the crosshead speed is adjusted to maintain the appropriate strain rate for each portion of the test. For example, a crosshead speed of 10"/min (25.4 cm/min) would be used in Steps 1 and 3 for a sample gauge length of 1.25" (31.7 mm).

For each of the Post Elongation Recovery Test and the Two Cycle Hysteresis Test, barrier cuffs from feminine pads should be removed from their respective articles. The removal should ensure that structurally, the barrier cuff, i.e. elastic and cover, are in-tact as much as possible. As such, removal methods should preferably not structurally modify the behavior of the elastic members and/or the cover. So, solvents utilized to dissolve glues for discrete cuffs should be carefully selected. For those barrier cuffs which are integral to the chassis, these barrier cuffs should be cut out of the chassis ensuring that the outboard most portions of adhesive attaching the elastic to the topsheet and/or backsheet is including in the portion being cut from the chassis. Samples are then prepared as noted above with regard to these methods.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:

1. A disposable absorbent article having a longitudinal axis and a lateral axis perpendicular to the longitudinal axis, the disposable absorbent article further comprising:
    a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet;
    a fastening adhesive disposed on a garment-facing surface of the chassis;
    a first cuff extending along the first longitudinal side edge; and
    a second cuff extending along the second longitudinal side edge, wherein the article has a flexibility factor of less than 220 and an average pad curl of less than 3.0 mm.

2. The disposable absorbent article of claim 1, wherein the average pad curl is less than 2 mm.

3. The disposable absorbent article of claim 1, wherein an average cross directional peak load is less than 160 grams force.

4. The disposable absorbent article of claim 3, wherein an average cross directional peak load is between about 30 to about 160 grams force.

5. The disposable absorbent article of claim 1, wherein the first cuff and the second cuff comprise a portion of the topsheet and the backsheet.

6. The disposable absorbent article of claim 1, wherein the first cuff comprises a first cover and the second cuff comprises a second cover, wherein first cover and second cover are discrete from the chassis of the absorbent article.

7. The disposable absorbent article of claim 6, wherein the first cover and the second cover are attached to the topsheet.

8. The disposable absorbent article of claim 1, wherein the flexibility factor is less than 212.

9. The disposable absorbent article of claim 1, wherein the flexibility factor is between 50 and 220.

10. The disposable absorbent article of claim 1, wherein the average pad curl is less than 2.0 mm.

11. The disposable absorbent article of claim 1, wherein the average pad curl is between 0.5 mm and 2.5 mm.

12. The disposable absorbent article of claim 1, wherein the average pad curl is between 1.0 mm and 2.0 mm.

13. The disposable absorbent article of claim 1, wherein the average pad curl is between 0.5 mm and 3.0 mm.

14. A disposable absorbent article having a longitudinal axis and a lateral axis perpendicular to the longitudinal axis, the disposable absorbent article further comprising:
   a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet;
   a fastening adhesive disposed on a garment-facing surface of the chassis;
   a first cuff extending along the first longitudinal side edge; and
   a second cuff extending along the second longitudinal side edge, wherein the article has a flexibility factor of less than 190 and an average pad curl of less than 4.0 mm.

15. The disposable absorbent article of claim 14, wherein the average pad curl is less than 3.0 mm.

16. The disposable absorbent article of claim 14, wherein the average pad curl is between 0.5 mm and 4.0 mm.

17. The disposable absorbent article of claim 14, wherein the average pad curl is between 1.0 mm and 3.0 mm.

18. The disposable absorbent article of claim 14, wherein the flexibility factor is less than 180.

19. The disposable absorbent article of claim 14, wherein the flexibility factor is between 50 and 190.

20. The disposable absorbent article of claim 14, wherein the first cuff and the second cuff comprise a portion of the topsheet and the backsheet.

21. The disposable absorbent article of claim 14, wherein the first cuff comprises a first cover and the second cuff comprises a second cover, wherein first cover and second cover are discrete from the chassis of the absorbent article.

22. The disposable absorbent article of claim 21, wherein the first cover and the second cover are attached to the topsheet.

23. A disposable absorbent article having a longitudinal axis and a lateral axis perpendicular to the longitudinal axis, the disposable absorbent article further comprising:
   a chassis having first and second longitudinal side edges extending generally parallel to the longitudinal axis, a pair of end edges joining the first and second longitudinal side edges on opposite ends of the chassis, the chassis further comprising a topsheet; a backsheet; and an absorbent core disposed between the topsheet and the backsheet;
   a fastening adhesive disposed on a garment-facing surface of the chassis;
   a first cuff extending along the first longitudinal side edge; and
   a second cuff extending along the second longitudinal side edge, wherein the article has an average pad curl (APC) that satisfies the following equation:

$$APC \leq (-0.0338 FF + 8.7879)$$

wherein APC is in mm and FF is a flexibility factor of the article.

24. The disposable absorbent article of claim 23, wherein the first cuff and the second cuff comprise a portion of the topsheet and the backsheet.

25. The disposable absorbent article of claim 23, wherein the first cuff comprises a first cover and the second cuff comprises a second cover, wherein first cover and second cover are discrete from the chassis of the absorbent article.

26. The disposable absorbent article of claim 25, wherein the first cover and the second cover are attached to the topsheet.

27. The disposable absorbent article of claim 23, wherein the average pad curl is less than 9.0 mm.

28. The disposable absorbent article of claim 27, wherein the average pad curl is between 0.5 mm and 9.0 mm.

29. The disposable absorbent article of claim 23, wherein the average pad curl is less than 7.0 mm.

30. The disposable absorbent article of claim 29, wherein the average pad curl is between 0.5 mm and 7.0 mm.

31. The disposable absorbent article of claim 23, wherein the average pad curl is between 0.5 mm and 3.0 mm.

32. The disposable absorbent article of claim 23, wherein the flexibility factor is less than 260.

33. The disposable absorbent article of claim 23, wherein the flexibility factor is less than 240.

* * * * *